US010245361B2

(12) United States Patent
Yanai et al.

(10) Patent No.: US 10,245,361 B2
(45) Date of Patent: Apr. 2, 2019

(54) IMPELLER SUSPENSION MECHANISM FOR HEART PUMP

(71) Applicant: TC1 LLC, Pleasanton, CA (US)

(72) Inventors: Masamichi Yanai, Ann Arbor, MI (US); Jason Nanna, Ypsilanti, MI (US)

(73) Assignee: TC1 LLC, Pleasanton, CA (US)

( * ) Notice: Subject to any disclaimer, the term of this patent is extended or adjusted under 35 U.S.C. 154(b) by 417 days.

(21) Appl. No.: 15/042,685

(22) Filed: Feb. 12, 2016

(65) Prior Publication Data

US 2016/0235900 A1 Aug. 18, 2016

Related U.S. Application Data

(60) Provisional application No. 62/115,741, filed on Feb. 13, 2015.

(51) Int. Cl.
*A61N 1/362* (2006.01)
*A61M 1/10* (2006.01)
(Continued)

(52) U.S. Cl.
CPC ........ *A61M 1/1036* (2014.02); *A61M 1/1015* (2014.02); *A61M 1/1017* (2014.02);
(Continued)

(58) Field of Classification Search
CPC .............. A61M 1/1036; A61M 1/1015; A61M 1/1017; A61M 1/1031; A61M 1/122;
(Continued)

(56) References Cited

U.S. PATENT DOCUMENTS 1,093,868 A 4/1914 Leighty
2,684,035 A 7/1954 Kemp
(Continued)

FOREIGN PATENT DOCUMENTS

CN 1347585 A 5/2002
CN 1462344 A 12/2003
(Continued)

OTHER PUBLICATIONS

European office action dated Oct. 31, 2016 for EP 10804230.0, all pages.
(Continued)

*Primary Examiner* — Lindsey G Wehrheim
(74) *Attorney, Agent, or Firm* — Kilpatrick Townsend & Stockton LLP

(57) ABSTRACT

A centrifugal blood pump includes a housing that defines an inlet passage, a chamber, and an outlet passage. The pump includes an impeller rotatably positioned in the chamber to transfer blood from the inlet passage through the chamber and to the outlet passage and magnetic members embedded in the impeller such that the impeller and the magnetic members rotate together within the chamber. The pump includes a motor to control movement of the impeller in the chamber. The motor is adjacent the chamber and separated from the chamber by a partition member. The pump includes an inner annular magnetic member and an outer annular magnetic member embedded in a side of the housing opposite the partition member. A first net magnetic force between the inner annular magnetic member and the magnetic members exhibits greater attraction than a second net magnetic force between the outer annular member and the magnetic members.

20 Claims, 15 Drawing Sheets

(51) Int. Cl.
*F04D 13/06* (2006.01)
*F04D 29/047* (2006.01)
*F04D 29/048* (2006.01)
*A61M 1/12* (2006.01)

(52) U.S. Cl.
CPC ....... *F04D 13/064* (2013.01); *F04D 13/0666* (2013.01); *F04D 29/047* (2013.01); *F04D 29/048* (2013.01); *A61M 1/101* (2013.01); *A61M 1/1031* (2014.02); *A61M 1/1086* (2013.01); *A61M 1/122* (2014.02)

(58) Field of Classification Search
CPC ................ A61M 1/1086; F04D 13/064; F04D 13/0666; F04D 29/047; F04D 29/048
See application file for complete search history.

(56) References Cited

U.S. PATENT DOCUMENTS

| | | |
|---|---|---|
| 3,023,334 A | 2/1962 | Burr et al. |
| 3,510,229 A | 5/1970 | Smith |
| 3,620,638 A | 11/1971 | Kaye et al. |
| 3,870,382 A | 3/1975 | Reinhoudt |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 6/1983 | Sugawara |
| 4,434,389 A | 2/1984 | Langley et al. |
| 4,507,048 A | 3/1985 | Belenger et al. |
| 4,528,485 A | 7/1985 | Boyd, Jr. |
| 4,540,402 A | 9/1985 | Aigner |
| 4,549,860 A | 10/1985 | Yakich |
| 4,645,961 A | 2/1987 | Maisky |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papatonakos |
| 4,779,614 A | 10/1988 | Moise |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,857,781 A | 8/1989 | Shih |
| 4,888,011 A | 12/1989 | Kung et al. |
| 4,895,557 A | 1/1990 | Moise et al. |
| 4,900,227 A | 2/1990 | Troup lin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,100,374 A | 3/1992 | Kageyama |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Ozaki et al. |
| 5,129,883 A | 7/1992 | Black |
| 5,145,333 A | 9/1992 | Smith |
| 5,147,186 A | 9/1992 | Buckholtz |
| 5,112,349 A | 12/1992 | Summers et al. |
| 5,190,528 A | 2/1993 | Fonger et al. |
| 5,201,679 A | 4/1993 | Velte et al. |
| 5,211,546 A | 5/1993 | Isaacson et al. |
| 5,229,693 A | 7/1993 | Futami et al. |
| 5,275,580 A | 1/1994 | Yamazaki |
| 5,290,227 A | 1/1994 | Pasque |
| 5,360,445 A | 1/1994 | Goldowsky |
| 5,290,236 A | 3/1994 | Mathewson |
| 5,300,112 A | 4/1994 | Barr |
| 5,306,295 A | 4/1994 | Kolff et al. |
| 5,312,341 A | 5/1994 | Turi |
| 5,313,128 A | 5/1994 | Robinson et al. |
| 5,332,374 A | 7/1994 | Kricker et al. |
| 5,346,458 A | 9/1994 | Afield |
| 5,350,283 A | 9/1994 | Nakazeki et al. |
| 5,354,331 A | 11/1994 | Schachar |
| 5,370,509 A | 12/1994 | Golding et al. |
| 5,376,114 A | 12/1994 | Jarvik |
| 5,385,581 A | 1/1995 | Bramm et al. |
| 5,405,383 A | 11/1995 | Barr |
| 5,449,342 A | 12/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,519,270 A | 5/1996 | Yamada et al. |
| 5,533,957 A | 9/1996 | Aldea |
| 5,569,111 A | 10/1996 | Cho et al. |
| 5,575,630 A | 11/1996 | Nakazawa et al. |
| 5,588,812 A | 12/1996 | Taylor et al. |
| 5,595,762 A | 1/1997 | Derrieu et al. |
| 5,611,679 A | 3/1997 | Ghosh et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,749,855 A | 12/1998 | Reitan |
| 5,843,129 A | 12/1998 | Larson et al. |
| 5,851,174 A | 12/1998 | Jarvik et al. |
| 5,853,394 A | 12/1998 | Tolkoff et al. |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Israelev |
| 5,941,813 A | 8/1999 | Sievers et al. |
| 5,945,753 A | 8/1999 | Maegawa et al. |
| 5,868,702 A | 9/1999 | Stevens et al. |
| 5,868,703 A | 9/1999 | Bertolero et al. |
| 5,947,703 A | 9/1999 | Nojiri et al. |
| 5,951,263 A | 9/1999 | Taylor et al. |
| 5,984,892 A | 11/1999 | Bedingham |
| 5,964,694 A | 12/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,083,260 A | 7/2000 | Aboul-Hosn et al. |
| 6,100,618 A | 8/2000 | Schoeb et al. |
| 6,058,593 A | 9/2000 | Siess |

(56) References Cited

U.S. PATENT DOCUMENTS

| | | |
|---|---|---|
| 6,123,659 A | 9/2000 | leBlanc et al. |
| 6,123,726 A | 9/2000 | Mori et al. |
| 6,139,487 A | 10/2000 | Siess |
| 6,086,527 A | 11/2000 | Talpade |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,179,773 B1 | 1/2001 | Prem et al. |
| 6,190,304 B1 | 2/2001 | Downey et al. |
| 6,200,260 B1 | 3/2001 | Bolling |
| 6,206,659 B1 | 3/2001 | Izraelev |
| 6,254,359 B1 | 3/2001 | Aber |
| 6,222,290 B1 | 4/2001 | Schob et al. |
| 6,227,797 B1 * | 5/2001 | Watterson ............ A61M 1/101 415/107 |
| 6,227,820 B1 | 5/2001 | Jarvik |
| 6,234,772 B1 | 5/2001 | Wampler et al. |
| 6,234,998 B1 | 5/2001 | Wampler |
| 6,247,892 B1 | 6/2001 | Kazatchkov et al. |
| 6,249,067 B1 | 6/2001 | Schob et al. |
| 6,264,635 B1 | 7/2001 | Wampler et al. |
| 6,268,675 B1 | 7/2001 | Amrhein |
| 6,276,831 B1 | 8/2001 | Takahashi et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,320,731 B1 | 11/2001 | Eeaves et al. |
| 6,245,007 B1 | 12/2001 | Bedingham et al. |
| 6,351,048 B1 | 2/2002 | Schob et al. |
| 6,355,998 B1 | 3/2002 | Schob et al. |
| 6,365,996 B2 | 4/2002 | Schob |
| 6,375,607 B1 | 4/2002 | Prem |
| 6,387,037 B1 | 5/2002 | Bolling et al. |
| 6,394,769 B1 | 5/2002 | Bearnson et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,522,093 B1 | 2/2003 | Hsu et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,595,762 B2 | 7/2003 | Khanwilkar et al. |
| 6,605,032 B2 | 8/2003 | Benkowski et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,641,378 B2 | 11/2003 | Davis et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,157 B2 | 4/2004 | Goldowsky |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,846,168 B2 | 1/2005 | Davis et al. |
| 6,860,713 B2 | 1/2005 | Hoover |
| 6,884,210 B2 | 4/2005 | Nose et al. |
| 6,935,344 B1 | 8/2005 | Aboul-Hosn et al. |
| 6,926,662 B2 | 9/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,048,681 B2 | 5/2006 | Tsubouchi et al. |
| 7,089,059 B1 | 8/2006 | Pless |
| 7,090,401 B2 | 8/2006 | Rahman et al. |
| 7,112,903 B1 | 9/2006 | Schob |
| 7,122,019 B1 | 10/2006 | Kesten et al. |
| 7,128,538 B2 | 10/2006 | Tsubouchi et al. |
| 7,027,875 B2 | 11/2006 | Siess et al. |
| 7,156,802 B2 | 1/2007 | Woodard et al. |
| 7,160,243 B2 | 1/2007 | Medvedev |
| 7,175,588 B2 | 2/2007 | Morello |
| 7,202,582 B2 | 4/2007 | Eckert et al. |
| 7,172,551 B2 | 6/2007 | Leasure |
| 7,241,257 B1 | 10/2007 | Ainsworth et al. |
| 7,284,956 B2 | 10/2007 | Nose et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,329,236 B2 | 12/2008 | Kesten et al. |
| 7,462,019 B1 | 12/2008 | Allarie et al. |
| 7,467,930 B2 | 12/2008 | Ozaki et al. |
| 7,470,246 B2 | 12/2008 | Mori et al. |
| 7,476,077 B2 | 1/2009 | Woodard et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,660,635 B1 | 2/2010 | Verness et al. |
| 7,699,586 B2 | 4/2010 | LaRose et al. |
| 7,748,964 B2 | 7/2010 | Yaegashi et al. |
| 7,731,675 B2 | 8/2010 | Aboul-Hosn et al. |
| 7,802,966 B2 | 9/2010 | Wampler et al. |
| 7,841,976 B2 | 11/2010 | McBride et al. |
| 7,862,501 B2 | 1/2011 | Woodard |
| 7,888,242 B2 | 2/2011 | Tanaka et al. |
| 7,934,909 B2 | 5/2011 | Nuesser et al. |
| 7,972,122 B2 | 7/2011 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,152,493 B2 | 4/2012 | LaRose et al. |
| 8,177,703 B2 | 5/2012 | Smith et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Mustafa et al. |
| 8,535,211 B2 | 9/2013 | Campbell et al. |
| 8,585,290 B2 | 11/2013 | Bauer |
| 8,686,674 B2 | 4/2014 | Bi et al. |
| 8,770,945 B2 | 7/2014 | Ozaki et al. |
| 8,821,365 B2 | 9/2014 | Ozaki et al. |
| 8,827,661 B2 | 9/2014 | Mori |
| 8,652,024 B1 | 10/2014 | Yanai et al. |
| 8,864,644 B2 | 10/2014 | Yomtov |
| 8,870,552 B2 | 10/2014 | Ayre et al. |
| 8,968,174 B2 | 3/2015 | Yanai et al. |
| 9,039,595 B2 | 5/2015 | Ayre et al. |
| 9,067,005 B2 | 6/2015 | Ozaki et al. |
| 9,068,572 B2 | 6/2015 | Ozaki et al. |
| 9,109,601 B2 | 8/2015 | Mori |
| 9,132,215 B2 | 9/2015 | Ozaki et al. |

(56) References Cited

U.S. PATENT DOCUMENTS

| | | |
|---|---|---|
| 9,133,854 B2 | 9/2015 | Okawa et al. |
| 9,371,826 B2 | 6/2016 | Yanai et al. |
| 9,381,285 B2 | 7/2016 | Ozaki et al. |
| 9,382,908 B2 | 7/2016 | Ozaki et al. |
| 9,410,549 B2 | 8/2016 | Ozaki et al. |
| 9,556,873 B2 | 1/2017 | Yanai et al. |
| 2001/0039369 A1 | 11/2001 | Terentiev |
| 2002/0051711 A1 | 5/2002 | Ozaki |
| 2002/0058994 A1 | 5/2002 | Hill et al. |
| 2002/0094281 A1 | 7/2002 | Khanwilkar et al. |
| 2002/0095210 A1 | 7/2002 | Finnegan et al. |
| 2003/0023302 A1 | 1/2003 | Moe et al. |
| 2003/0045772 A1 | 3/2003 | Reich et al. |
| 2003/0072656 A1 | 4/2003 | Niwatsukino et al. |
| 2003/0144574 A1 | 7/2003 | Heilman et al. |
| 2003/0199727 A1 | 10/2003 | Burke et al. |
| 2003/0236488 A1 | 12/2003 | Novak |
| 2003/0236490 A1 | 12/2003 | Novak |
| 2004/0007515 A1 | 1/2004 | Geyer |
| 2004/0015232 A1 | 1/2004 | Shu et al. |
| 2004/0024285 A1 | 2/2004 | Muckter |
| 2004/0030381 A1 | 2/2004 | Shu |
| 2004/0064012 A1 | 4/2004 | Yanai |
| 2004/0143151 A1 | 7/2004 | Mori et al. |
| 2004/0145337 A1 | 7/2004 | Morishita |
| 2004/0152944 A1 | 8/2004 | Medvedev et al. |
| 2004/0171905 A1 | 9/2004 | Yu et al. |
| 2004/0210305 A1 | 10/2004 | Shu et al. |
| 2004/0215050 A1 | 10/2004 | Morello |
| 2004/0263341 A1 | 12/2004 | Enzinna |
| 2005/0004418 A1 | 1/2005 | Morello |
| 2005/0008496 A1 | 1/2005 | Tsubouchi et al. |
| 2005/0025630 A1 | 2/2005 | Ayre et al. |
| 2005/0043665 A1 | 2/2005 | Vinci et al. |
| 2005/0073273 A1 | 4/2005 | Maslov et al. |
| 2005/0089422 A1 | 4/2005 | Ozaki et al. |
| 2005/0131271 A1 | 6/2005 | Benkowski et al. |
| 2005/0141887 A1 | 6/2005 | Lelkes |
| 2005/0194851 A1 | 9/2005 | Eckert et al. |
| 2005/0261542 A1 | 11/2005 | Abe et al. |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2006/0127227 A1 | 6/2006 | Mehlhorn et al. |
| 2007/0073393 A1 | 3/2007 | Kung et al. |
| 2007/0078293 A1 | 4/2007 | Shambaugh, Jr. |
| 2007/0095648 A1 | 5/2007 | May et al. |
| 2007/0114961 A1 | 5/2007 | Schwarzkopf |
| 2007/0134993 A1 | 6/2007 | Tamez et al. |
| 2007/0189648 A1 | 8/2007 | Kita et al. |
| 2007/0213690 A1 | 9/2007 | Phillips et al. |
| 2007/0231135 A1 | 10/2007 | Wampler et al. |
| 2007/0282298 A1 | 12/2007 | Mason |
| 2007/0297923 A1 | 12/2007 | Tada |
| 2008/0007196 A1 | 1/2008 | Tan et al. |
| 2008/0021394 A1 | 1/2008 | La Rose et al. |
| 2008/0030895 A1 | 2/2008 | Obara et al. |
| 2008/0119777 A1 | 5/2008 | Vinci et al. |
| 2008/0124231 A1 | 5/2008 | Yaegashi |
| 2008/0183287 A1 | 7/2008 | Ayre |
| 2008/0211439 A1 | 9/2008 | Yokota et al. |
| 2008/0281146 A1 | 11/2008 | Morello |
| 2009/0041595 A1 | 2/2009 | Garzaniti et al. |
| 2009/0060743 A1 | 3/2009 | McBride et al. |
| 2009/0074336 A1 | 3/2009 | Engesser et al. |
| 2009/0099406 A1 | 4/2009 | Salmonsen et al. |
| 2009/0171136 A1 | 7/2009 | Shambaugh, Jr. |
| 2009/0257693 A1 | 10/2009 | Aiello |
| 2009/0318834 A1 | 12/2009 | Fujiwara et al. |
| 2010/0168534 A1 | 7/2010 | Matsumoto et al. |
| 2010/0185280 A1 | 7/2010 | Ayre et al. |
| 2010/0222634 A1 | 9/2010 | Poirier |
| 2010/0234835 A1 | 9/2010 | Horikawa et al. |
| 2010/0256440 A1 | 10/2010 | Maher |
| 2010/0262039 A1 | 10/2010 | Fujiwara et al. |
| 2010/0266423 A1 | 10/2010 | Gohean et al. |
| 2010/0305692 A1 | 12/2010 | Thomas et al. |
| 2010/0324465 A1 | 12/2010 | Vinci et al. |
| 2011/0015732 A1 | 1/2011 | Kanebako |
| 2011/0112354 A1 | 5/2011 | Nishimura et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0129373 A1 | 6/2011 | Mori |
| 2011/0160519 A1 | 6/2011 | Arndt et al. |
| 2011/0218383 A1 | 9/2011 | Broen et al. |
| 2011/0218384 A1 | 9/2011 | Bachman et al. |
| 2011/0218385 A1 | 9/2011 | Bolyare et al. |
| 2011/0237978 A1 | 9/2011 | Fujiwara et al. |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0022645 A1 | 1/2012 | Burke |
| 2012/0035411 A1 | 2/2012 | LaRose et al. |
| 2012/0078030 A1 | 3/2012 | Bourque |
| 2012/0078031 A1 | 3/2012 | Burke et al. |
| 2012/0095281 A1 | 4/2012 | Reichenbach et al. |
| 2012/0130152 A1 | 5/2012 | Ozaki et al. |
| 2012/0226350 A1 | 9/2012 | Ruder et al. |
| 2012/0243759 A1 | 9/2012 | Fujisawa |
| 2012/0245681 A1 | 9/2012 | Casas et al. |
| 2012/0253103 A1 | 10/2012 | Jarvik |
| 2012/0308363 A1 | 12/2012 | Ozaki et al. |
| 2013/0030240 A1 | 1/2013 | Schima et al. |
| 2013/0121821 A1 | 5/2013 | Ozaki et al. |
| 2013/0158521 A1 | 6/2013 | Sobue |
| 2013/0170970 A1 | 7/2013 | Ozaki et al. |
| 2013/0178694 A1 | 7/2013 | Jeffery et al. |
| 2013/0225909 A1 | 8/2013 | Dormanen et al. |
| 2013/0243623 A1 | 9/2013 | Okawa et al. |
| 2013/0289334 A1 | 10/2013 | Badstibner et al. |
| 2013/0331711 A1 | 12/2013 | Mathur et al. |
| 2014/0030122 A1 | 1/2014 | Ozaki et al. |
| 2014/0066690 A1 | 3/2014 | Siebenhaar et al. |
| 2014/0066691 A1 | 3/2014 | Siebenhaar |
| 2014/0100413 A1 | 4/2014 | Casas et al. |
| 2014/0107399 A1 | 4/2014 | Spence |
| 2014/0142367 A1 | 5/2014 | Ayre et al. |
| 2014/0155682 A1 | 6/2014 | Jeffery et al. |
| 2014/0200389 A1 | 7/2014 | Yanai et al. |
| 2014/0205467 A1 | 7/2014 | Yanai et al. |
| 2014/0241904 A1 | 8/2014 | Yanai et al. |
| 2014/0275721 A1 | 9/2014 | Yanai et al. |
| 2014/0275727 A1 | 9/2014 | Bonde et al. |
| 2014/0296615 A1 | 10/2014 | Franano |
| 2014/0309481 A1 | 10/2014 | Medvedev et al. |
| 2014/0314597 A1 | 10/2014 | Allaire et al. |
| 2014/0323796 A1 | 10/2014 | Medvedev et al. |
| 2014/0343352 A1 | 11/2014 | Ardt et al. |
| 2015/0017030 A1 | 1/2015 | Ozaki et al. |
| 2015/0023803 A1 | 1/2015 | Fritz et al. |
| 2015/0078936 A1 | 3/2015 | Mori |
| 2015/0306290 A1 | 10/2015 | Rosenberg et al. |
| 2015/0367048 A1 | 12/2015 | Brown et al. |
| 2015/0374892 A1 | 12/2015 | Yanai et al. |
| 2016/0058929 A1 | 3/2016 | Medvedev et al. |
| 2016/0058930 A1 | 3/2016 | Medvedev et al. |
| 2016/0228628 A1 | 8/2016 | Medvedev et al. |
| 2016/0235898 A1 | 8/2016 | Yanai et al. |
| 2016/0235899 A1 | 8/2016 | Yu et al. |
| 2016/0281720 A1 | 9/2016 | Yanai et al. |
| 2016/0281728 A1 | 9/2016 | Ozaki et al. |

FOREIGN PATENT DOCUMENTS

| | | |
|---|---|---|
| CN | 102239334 A | 11/2011 |
| CN | 102341600 A | 2/2012 |
| EP | 2945662 B1 | 9/1999 |
| EP | 971212 A | 1/2000 |
| EP | 1113117 A2 | 7/2001 |
| EP | 1327455 A | 7/2003 |
| EP | 1430919 A1 | 6/2004 |
| EP | 1598087 A2 | 3/2005 |

(56) References Cited

FOREIGN PATENT DOCUMENTS

| | | |
|---|---|---|
| EP | 1526286 A1 | 4/2005 |
| EP | 1495773 A3 | 11/2006 |
| EP | 2292282 A1 | 3/2011 |
| EP | 2298375 A1 | 3/2011 |
| EP | 2372160 A1 | 10/2011 |
| EP | 2405140 A1 | 1/2012 |
| EP | 2405141 A1 | 1/2012 |
| EP | 2461465 A1 | 6/2012 |
| EP | 2538086 A1 | 12/2012 |
| EP | 2554191 A1 | 2/2013 |
| EP | 2594799 A1 | 5/2013 |
| EP | 2618001 A1 | 7/2013 |
| EP | 2693609 A1 | 2/2014 |
| EP | 2948202 A1 | 12/2015 |
| EP | 2961987 A1 | 1/2016 |
| EP | 3013385 A2 | 5/2016 |
| JP | 58/9535 | 1/1983 |
| JP | 61/293146 | 12/1986 |
| JP | H02-007780 U | 1/1990 |
| JP | H02-033590 U | 3/1990 |
| JP | 04/091396 A | 3/1992 |
| JP | 04/148094 A | 5/1992 |
| JP | 05/021197 U | 3/1993 |
| JP | 06/014538 U | 2/1994 |
| JP | 06/053790 U | 7/1994 |
| JP | 2006/070476 | 9/1994 |
| JP | 2006/245455 | 9/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004/166401 A | 6/2004 |
| JP | 2004/209240 A | 7/2004 |
| JP | 2004/332566 A | 11/2004 |
| JP | 2004/346925 A | 12/2004 |
| JP | 2005/094955 | 4/2005 |
| JP | 2005/127222 A | 5/2005 |
| JP | 2005/245138 | 9/2005 |
| JP | 2005/270345 A | 10/2005 |
| JP | 2005/270415 A | 10/2005 |
| JP | 2005/287599 A | 10/2005 |
| JP | 2007/002885 A | 1/2007 |
| JP | 2007/043821 | 2/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/011611 | 1/2008 |
| JP | 2008/104278 | 5/2008 |
| JP | 2008/132131 | 6/2008 |
| JP | 2008/99453 | 8/2008 |
| JP | 2008/193838 | 8/2008 |
| JP | 2008/297997 A | 12/2008 |
| JP | 2008/301634 | 12/2008 |
| JP | 2006/167173 A | 6/2009 |
| JP | 2006/254619 | 9/2009 |
| JP | 2010/133381 A | 6/2010 |
| JP | 2010/136863 A | 6/2010 |
| JP | 2010/203398 A | 9/2010 |
| JP | 2010/209691 A | 9/2010 |
| JP | 2011/169166 A | 9/2011 |
| JP | 2012/021413 | 2/2012 |
| JP | 2012/062790 A | 3/2012 |
| JP | 5171953 B2 | 3/2013 |
| JP | 5572832 B2 | 8/2014 |
| JP | 5656835 B2 | 1/2015 |
| WO | 1993/07388 A1 | 4/1993 |
| WO | 94/14226 | 6/1994 |
| WO | 1996/31934 | 10/1996 |
| WO | 1997/42413 A1 | 11/1997 |
| WO | 2000/64509 A1 | 11/2000 |
| WO | 2004/098677 A1 | 11/2004 |
| WO | 2005/011087 A1 | 2/2005 |
| WO | 2005/028000 A1 | 3/2005 |
| WO | 2005/034312 A2 | 4/2005 |
| WO | 2009/157408 A1 | 12/2009 |
| WO | 2010/067682 A1 | 6/2010 |
| WO | 2010/101082 A1 | 9/2010 |
| WO | 2010/101107 A1 | 9/2010 |
| WO | 2011/013483 A1 | 2/2011 |
| WO | 2012/036059 A1 | 3/2012 |
| WO | 2012/040544 A1 | 3/2012 |
| WO | 2012/047550 A1 | 4/2012 |
| WO | 2012/132850 A1 | 10/2012 |
| WO | 2014/113533 A1 | 7/2014 |
| WO | 2014/116676 A1 | 7/2014 |
| WO | 2014/133942 A1 | 9/2014 |
| WO | 2014/179271 A2 | 11/2014 |
| WO | 2016/033131 A1 | 3/2016 |
| WO | 2016/033133 A1 | 3/2016 |
| WO | 2016/130846 A1 | 8/2016 |
| WO | 2016/130944 A1 | 8/2016 |
| WO | 2016/130955 A1 | 8/2016 |

OTHER PUBLICATIONS

European Office Action issued in Application No. EP 11825062 dated Jul. 19, 2016, all pages.
Gieras, et al., "Advancements in Electric Machines", Nov. 14, 2008, pp. 43-48.
International Search Report and Written Opinion of PCT/US2016/062284, dated Feb. 24, 2017, all pages.
European office action dated Jul. 22, 2016 for European Patent Application No. EP 09770118.9, all pages.
European office action dated Sep. 8, 2016 for EP 14741174, all pages.
Extended European Search Report for EP 14 74 3371 dated Sep. 29, 2016, all pages.
International Search Report and Written Opinion of PCT/US2016/017812 dated Jun. 7, 2016, all pages.
International Search Report and Written Opinion of PCT/US2016/017864, dated Jun. 8, 2016, all pages.
Decision to Grant for JP 2013-507344 dated Jun. 14, 2016, all pages.
International Search Report and Written Opinion of PCT/US2015/046844, dated Oct. 27, 2015, all pages.
International Search Report and Written Opinion of PCT/US2015/046846, dated Oct. 27, 2015, all pages.
European office action dated Jan. 27, 2016 for EP 10804230.0, all pages.
Extended European Search Report dated Feb. 4, 2016 in European Patent Application No. EP 12764433.4, filed Mar. 12, 2012, all pages.
International Preliminary Report on Patentability dated Jul. 30, 2015 for International Patent Application No. PCT/US2014/011786, filed on Jan. 16, 2014, all pages.
International Search Report and Written Opinion of PCT/US2014/012511, dated May 147, 2014, all pages.
International Search Report and Written Opinion of PCT/US2014/017932, dated Jun. 16, 2014, all pages.
International Preliminary Report on Patentability dated Sep. 11, 2015 for International Patent Application No. PCT/US2014/017932, filed on Feb. 24, 2014, all pages.
International Search Report and Written Opinion of PCT/US2014/035798, dated Feb. 11, 2016, all pages.
International Search Report and Written Opinion of PCT/US2016/017611, dated May 16, 2016, all pages.
International Search Report and Written Opinion of PCT/US2016/017791, dated May 16, 2016, all pages.
Japanese office action dated Dec. 8, 2015 JP 2013-507344, all pages.
Asama, J., et al., "A Compact Highly Efficient and Low Hemolytic Centrifugal Blood Pump With a Magnetically Levitated Impeller", Artificial Organs, vol. 30, No. 3, Mar. 1, 2006 (Mar. 1, 2006), pp. 160-167.

(56) References Cited

OTHER PUBLICATIONS

Asama, J., et al.,"A New Design for a Compact Centrifugal Blood Pump with a Magnetically Levitated Rotor", Asaio Jopurnal, vol. 50, No. 6, Nov. 1, 2004 (Nov. 1, 2004), pp. 550-556.
Asama, et al., "Suspension Performance of a Two-Axis Actively Regulated Consequent-Pole Bearingless Motor," IEEE Transactions on Energy Conversion, vol. 28, No. 4, Dec. 2013, 8 pages.
European Search report Issued in European Patent Application No. 10748702.7, dated Apr. 2, 2013.
Extended European Search Report issued in European Patent Application No. EP 10748677.1, dated Nov. 19, 2012.
Extended European Search Report issued in European Patent Application No. EP 11825062.0, dated Jun. 18, 2015, all pages.
Extended European Search Report issued in European Patent Application No. EP 11806627.3, dated Oct. 8, 2014, all pages.
Extended European Search Report dated Mar. 26, 2015 in European Patent Application No. EP 09770118.9 filed Jun. 22, 2009, all pages.
International Search Report (PCT/ISA/210) dated Jul. 14, 2009, by Japanese Patent Office as the International Searching Authority for International Application No. PCT/JP2009/061318.
International Search Report and Written Opinion issued in PCT/JP2011/050925, dated Apr. 12, 2011.
International Search Report and Written Opinion issued in PCT/JP2011/054134, dated Apr. 12, 2011.
International Search Report and Written Opinion issued in PCT/JP2011/064768, dated Sep. 13, 2011.
International Search Report and Written Opinion issued in PCT/JP2011/070450, dated Dec. 13, 2011.
International Search Report and Written Opinion of PCT/US2014/012448 dated Feb. 19, 2014, all pages.
International Search Report and Written Opinion of PCT/US2014/011786 dated May 5, 2014, all pages.
International Search Report and Written Opinion of PCT/US2014/012502 dated May 9, 2014, all pages.
International Search Report and Written Opinion of PCT/US2014/012511 dated May 14, 2014, all pages.
International Preliminary Report on Patentability dated Aug. 6, 2015 for International Patent Application No. PCT/US2014/012511 filed on Jan. 22, 2014, all pages.
International Preliminary Report on Patentability dated Aug. 6, 2015 for International Patent Application No. PCT/US2014/012502 filed on Jan. 22, 2014, all pages.
International Preliminary Report on Patentability dated Feb. 25, 2016 for International Patent Application No. PCT/US2014/035798 filed on Apr. 29, 2014, all pages.
Kosaka, et al., "Operating Point Control Systemt for a Continuous Flow Artificial Heart: In Vitro Study," Asaio Journal 2003, all pages.
Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.
Supplementary European Search Report issued in European Application No. 10748702.7, dated Apr. 2, 2013, all pages.
Sandtner, J., et al., "Electrodynamic Passive Magnetic Bearing with Planar Halbach Arrays", Aug. 6, 2004 (Aug. 6, 2004), retrieved from the internet: <http://www.silphenix.ch/lexington.pdf>, all pages.
Supplementary European Search Report issued in European Application No. 09831788.6, dated Jan. 7, 2013, 7 pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," Asaio Journal, 1993, 7 pages.

* cited by examiner

IMPELLER SUSPENSION MECHANISM FOR HEART PUMP

CROSS-REFERENCES TO RELATED APPLICATIONS

This application claims priority to U.S. Provisional Application No. 62/115,741, filed Feb. 13, 2015 and entitled "IMPELLER SUSPENSION MECHANISM FOR HEART PUMP," which is hereby incorporated by reference in its entirety.

BACKGROUND OF THE INVENTION

Conventional heart pumps utilize magnetic elements and/or hydrostatic bearings within a housing of the pump to compensate attractive forces produced by a stator motor to maintain an impeller of the pump in a desired position within a chamber of the pump. Such magnetic attractive forces from the magnetic elements provide negative stiffness. This negative stiffness increases as a distance between the magnetic elements within the housing and magnets on the impeller becomes shorter. Any tilt of the impeller will decrease a gap between the impeller and the wall of the chamber at an outer edge of the impeller. At low impeller speeds, hydrodynamic bearing forces are sufficient to maintain this gap. However, in conventional pump designs, at high speeds the impeller tends to tilt, resulting in a decrease of a size of the gap near the outer edges of the impeller.

BRIEF SUMMARY OF THE INVENTION

In one aspect, a centrifugal blood pump is provided. The pump may include a housing that defines an inlet passage, a chamber, and an outlet passage. The pump may also include an impeller rotatably positioned in the chamber to transfer blood from the inlet passage through the chamber and to the outlet passage. The impeller may include an inner portion and an outer portion. The pump may further include a plurality of impeller magnets embedded in the impeller such that the impeller and the plurality of impeller magnets rotate together within the chamber. The plurality of impeller magnets may include an inner impeller magnet and an outer impeller magnet relative to a central axis of the impeller. The pump may include a motor to control movement of the impeller in the chamber. The motor may be positioned adjacent the chamber and separated from the chamber by a partition member. The pump may also include an inner annular magnetic member embedded in a wall of the housing opposite the partition member and an outer annular magnetic member embedded in the wall of the housing opposite the partition member. A first net magnetic force between the inner annular magnetic member and the inner impeller magnet may exhibit greater attraction than a second net magnetic force between the outer annular member and the outer impeller magnet.

In another aspect, a centrifugal blood pump may include a housing that defines an inlet passage, a chamber, and an outlet passage. The pump may also include an impeller rotatably positioned in the chamber to transfer blood from the inlet passage through the chamber and to the outlet passage. The pump may further include a plurality of impeller magnets embedded in the impeller such that the impeller and the plurality of impeller magnets rotate together within the chamber. The pump may include a motor to control movement of the impeller in the chamber. The motor may be positioned adjacent the chamber and separated from the chamber by a partition member. The pump may further include at least one annular magnetic member embedded in a wall of the housing opposite the partition member. A first net magnetic force between the at least one annular magnetic member and a proximal portion the plurality of impeller magnets may exhibit greater attraction than a second net magnetic force between the at least one annular magnetic member and a distal portion of the plurality of impeller magnets. The proximal portion and the distal portion may be relative to a central axis of the impeller.

In another aspect, a centrifugal blood pump may include a housing that defines an inlet passage, a chamber, and an outlet passage. The pump may also include an impeller rotatably positioned in the chamber to transfer blood from the inlet passage through the chamber and to the outlet passage. The impeller may include an inner portion and an outer portion relative to a central axis of the impeller. The pump may further include at least one impeller magnet embedded in the impeller such that the impeller and at least one magnetic member rotate together within the chamber. The pump may include a motor to control movement of the impeller in the chamber. The motor may be positioned adjacent the chamber and separated from the chamber by a partition member. The pump may also include at least one annular magnetic member embedded in a side of the housing opposite the partition member. A first force exhibited on the inner portion may have a greater attraction than a second force exhibited on the outer portion of the impeller. The first force and the second force may each result from interactions between the at least one impeller magnet and the at least one annular magnetic member.

DETAILED DESCRIPTION OF THE INVENTION

Figure 1:
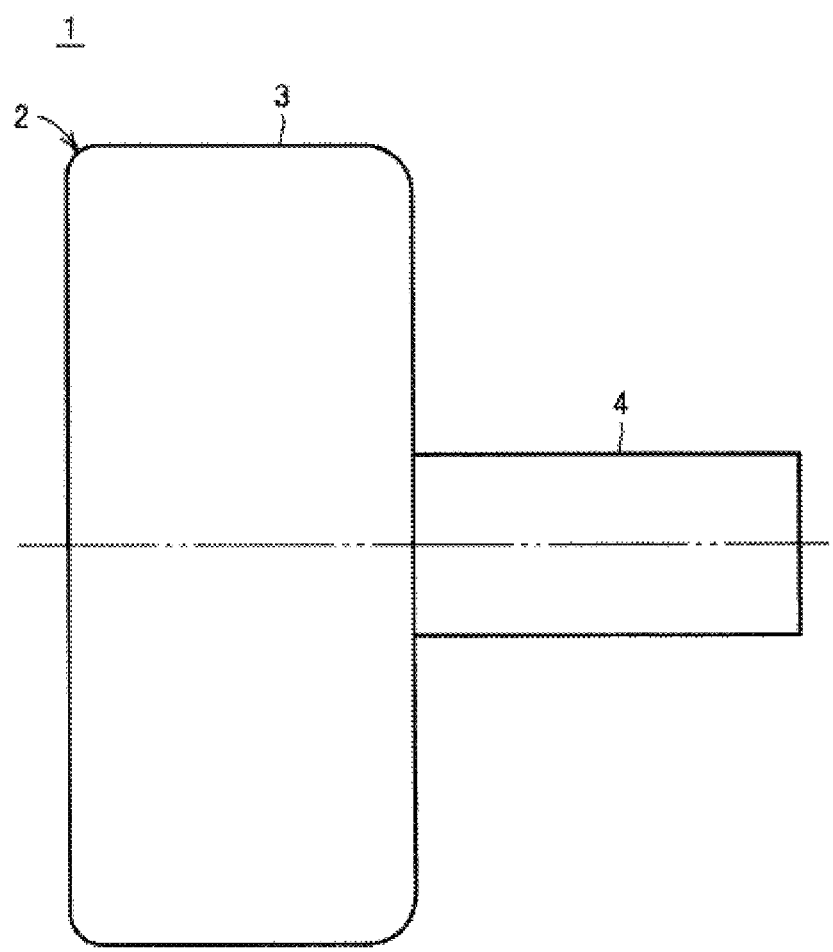
FIG. 1 shows an example centrifugal blood pump according to the disclosure.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth herein.

Specific details are given in the following description to provide a thorough understanding of the embodiments. However, it will be understood by one of ordinary skill in the art that the embodiments may be practiced without these specific details. For example, with regard to any specific embodiment discussed herein, any one or more details may or may not be present in all versions of that embodiment. Likewise, any detail from one embodiment may or may not be present in any particular version of another embodiment discussed herein. Additionally, well-known circuits, systems, processes, algorithms, structures, and techniques may be shown without unnecessary detail in order to avoid obscuring the embodiments. The absence of discussion of any particular element with regard to any embodiment herein shall be construed to be an implicit contemplation by the disclosure of the absence of that element in any particular version of that or any other embodiment discussed herein.

The present disclosure is directed to, among other things, minimizing or preventing a decrease in gap size at high impeller speeds between the outer edge of the impeller and the inner wall of a chamber of a blood pump. Some aspects of the disclosure are directed to reducing the risk of undesirable tilting of the impeller and/or improving the overall stability of the impeller during operation. Embodiments maintain an appropriately sized gap through all impeller speeds by decreasing the net attractive magnetic force on an outer portion of the impeller, or by having a lower net attractive force on an outer portion of the impeller than an inner portion. Although the feature or aspects of the present disclosure are not limited to a specific type of mechanical blood pump, an example of a blood pump in which embodiments of maintaining an appropriate gap size may be practiced is shown and described in connection with FIGS. 1-7. As will be understood by one of skill from the description herein, some of the features described increase a stabilizing force on the impeller over conventional non-contact pump bearings, in various respects, along the tilt axis.

In FIGS. 1-7, an exemplary centrifugal blood pump is shown that includes a pump unit 1 that includes a housing 2 made of a nonmagnetic material. Housing 2 includes a cylindrical body portion 3, a cylindrical blood inlet port 4 that extends from one end surface of body portion 3, and a cylindrical blood outlet port 5 that extends from another end surface of body portion 3. Blood outlet port 5 extends in a tangential direction of the outer circumferential surface of body portion 3.

Figure 2:
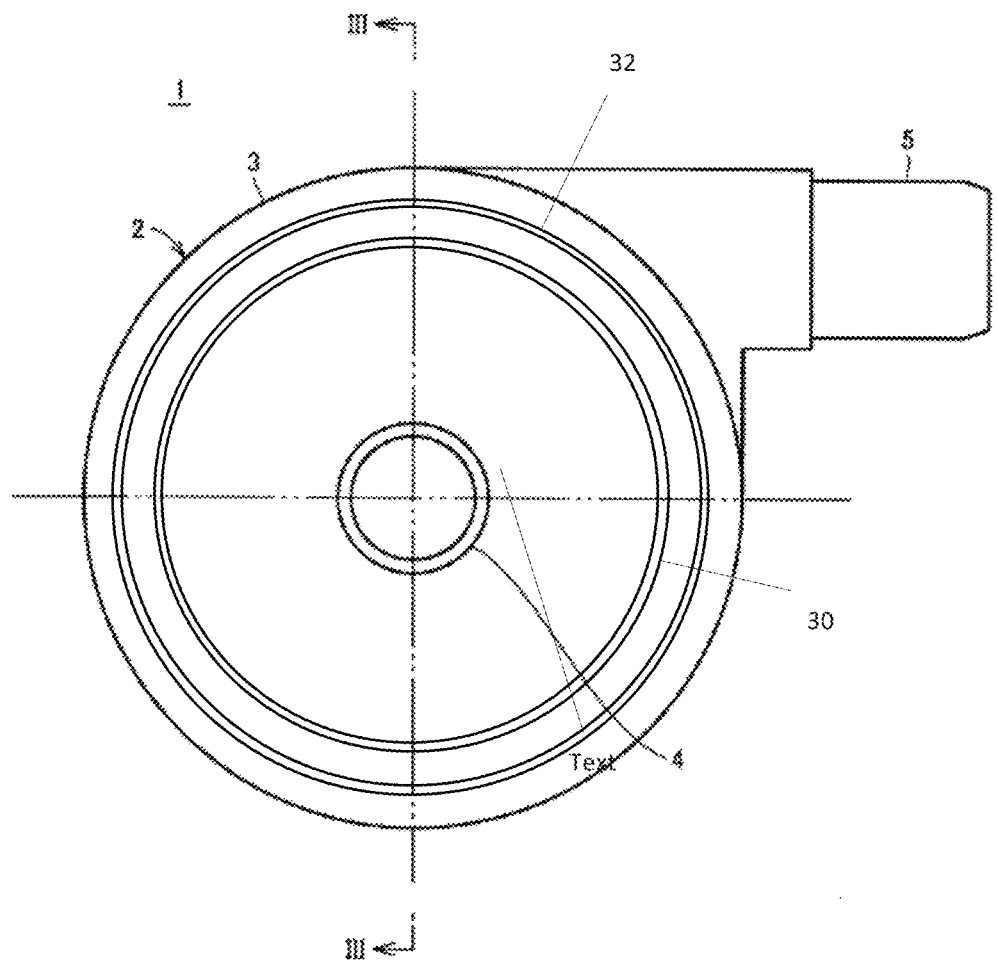
FIG. 2 shows the blood pump of FIG. 1 in an alternate view.

As shown in FIG. 2, a position of one or more annular shaped magnetic members is shown. In some embodiments, pump unit 1 may include an inner annular magnetic member 30 and an outer annular magnetic member 32. Other embodiments may include one annular magnetic member or more than two annular magnetic members. The annular magnetic members 30 and 32 may each be formed from a single ring-shaped magnetic member, or may be formed from a number of magnetic members arranged in an annular pattern.

Figure 3:
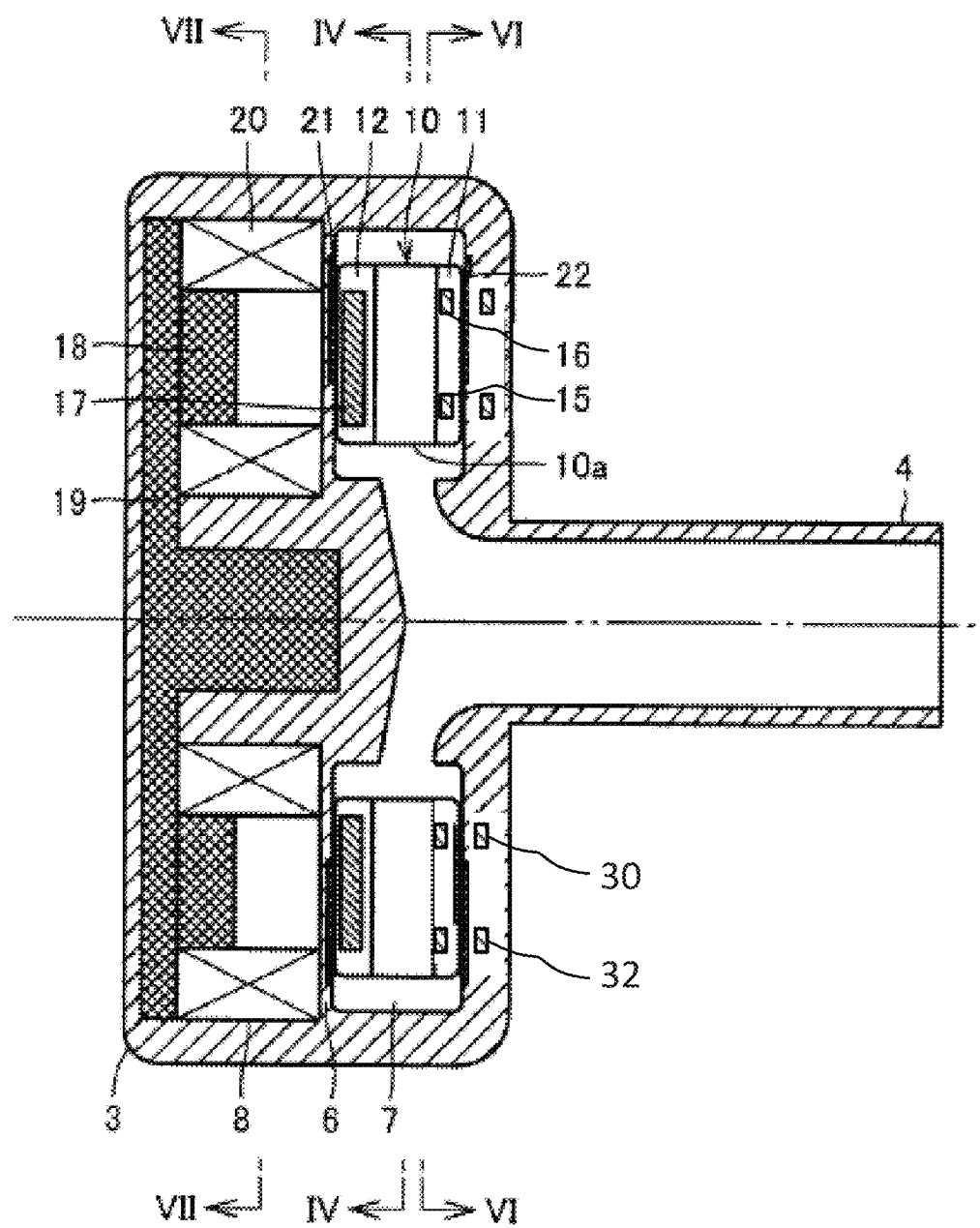
FIG. 3 shows a cross-section of the blood pump of FIG. 1.
Figure 4:
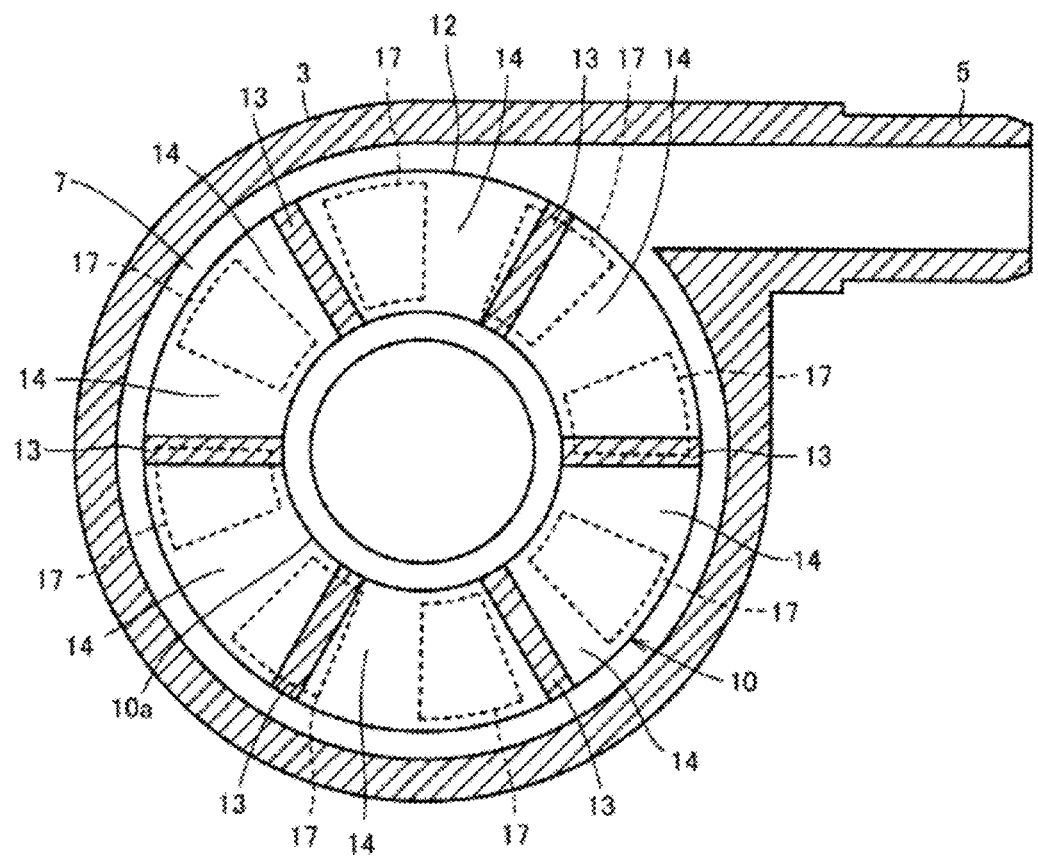
FIG. 4 shows another cross-section of the blood pump of FIG. 1.

As shown in FIG. 3, a blood chamber 7 and a motor chamber 8 are partitioned from each other by a dividing wall 6 within housing 2. Blood chamber 7, as shown in FIGS. 3-4, includes a rotatable disc-shaped impeller 10 having a through hole 10a in a center thereof. Impeller 10 includes two shrouds 11, 12 in an annular shape, and a plurality (e.g., six) of vanes 13 formed between two shrouds 11 and 12. Shroud 11 is arranged on the blood inlet port 4 side, and shroud 12 is arranged on the dividing wall 6 side. Shrouds 11, 12 and vanes 13 are made of a nonmagnetic material.

A plurality (six in this case) of blood passages 14 are formed between two shrouds 11 and 12 and are partitioned from one another by the plurality of vanes 13. As shown in FIG. 4, blood passage 14 is in communication with through hole 10a at the center of impeller 10, and extends with through hole 10a of impeller 10 as a starting point to an outer circumference such that blood passage 14 gradually increases in width. In other words, each vane 13 is formed between two adjacent blood passages 14. In the first embodiment, the plurality of vanes 13 are provided at regular angular intervals, and each has the same shape. Thus, the plurality of blood passages 14 are provided at regular angular intervals and has the same shape.

When impeller 10 is driven to rotate, blood that has flowed in through blood inlet port 4 is delivered by centrifugal force from through hole 10a to an outer circumferential portion of impeller 10 via blood passages 14, and flows out through blood outlet port 5. It is contemplated that the blood inlet port 4 may be configured and/or arranged to minimize or prevent the formation of thrombosis within (i.e., internal) the blood inlet port 4, and also to minimize turbulence at a fluid interface between the blood inlet port 4 and the blood chamber 7.

A plurality of permanent magnets may be embedded in shroud 11. For example, an inner magnet 15 and an outer magnet 16 may be included in shroud 11. One or more annular magnetic members may be embedded in an inner wall of blood chamber 7 facing shroud 11. For example, inner annular magnetic member 30 and outer annular magnetic member may be embedded in the inner wall. The annular magnetic members 30 and 32 may be permanent magnets or may be electromagnetic elements. Either a soft magnetic element or a hard magnetic element may be used as the annular magnetic members 30 and/or 32.

The annular magnetic members 30 and 32 may each be formed as a single permanent magnet or as a plurality of permanent magnets. If a single permanent magnet is provided, the permanent magnet is formed in an annular or ring shape. If a plurality of permanent magnets are provided, the plurality of permanent magnets may be arranged at regular angular intervals along the same circle. While described as annular magnetic members, it will be appreciated that each of the magnetic members described herein may be formed from one or more magnets, and may be in any non-annular arrangement, such as other symmetrical shapes. In some embodiments, the inner annular magnetic member 30 may have a greater net attractive force with the inner magnet 15 than the net attractive force between the outer annular magnetic member 32 and the outer magnet 16. Such a configuration may decrease the tilt of the impeller, especially at high impeller speeds, thus maintaining a size of the gap between the outer edge of the impeller and the housing wall.

As shown in FIG. 4, a plurality (e.g., nine) of permanent magnets 17 are embedded in shroud 12. The plurality of permanent magnets 17 are arranged with a gap therebetween at regular angular intervals along the same circle such that magnetic polarities of adjacent permanent magnets 17 are different from each other. In other words, permanent magnet 17 having the N-pole toward motor chamber 8 and permanent magnet 17 having the S-pole toward motor chamber 8 are alternately arranged with a gap therebetween at regular angular intervals along the same circle.

Figure 7:
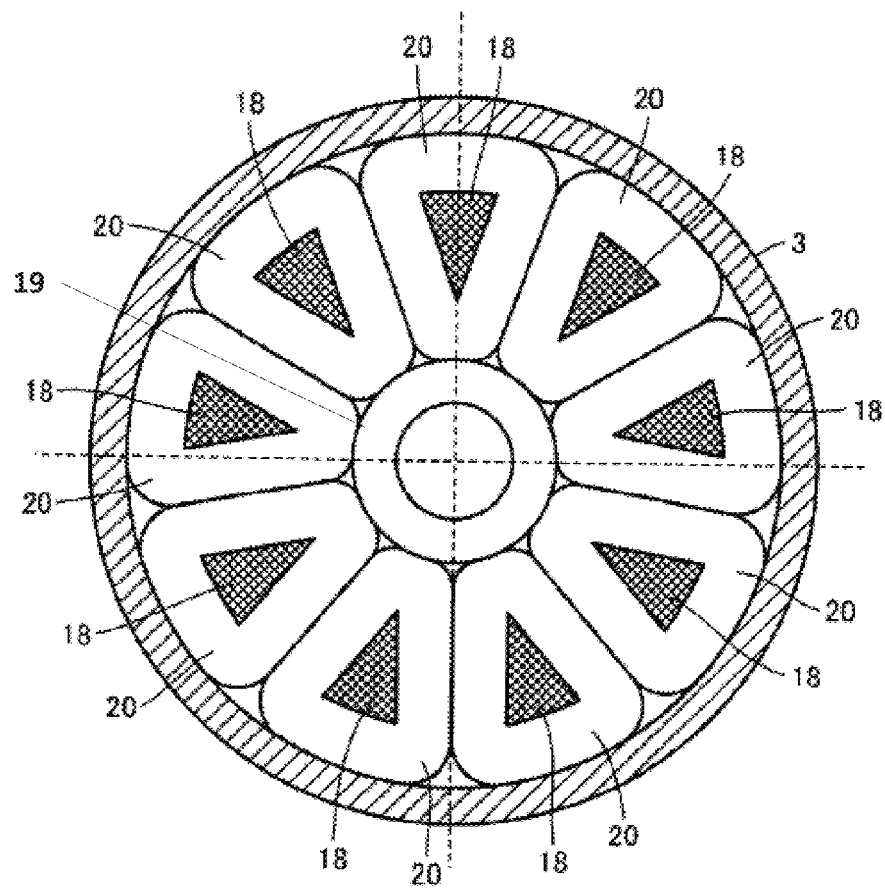
FIG. 7 shows yet another cross-section of the blood pump of FIG. 1.

As shown in FIG. 3 and FIG. 7, a plurality (e.g., nine) of magnetic elements 18 are provided in motor chamber 8. The plurality of magnetic elements 18 are arranged at regular angular intervals along the same circle to face the plurality of permanent magnets 17 in impeller 10. A base end of each of the plurality of magnetic elements 18 is joined to one disc-shaped magnetic element 19. A coil 20 is wound around each magnetic element 18. In the direction of a central axis of impeller 10, the length of magnetic element 18 is shorter than that of coil 20. That is, when an axial length of magnetic element 18 is expressed as x and an axial length of coil 20 is expressed as L relative to the surface of disc-shaped magnetic element 19, a relationship of 0<x<L is satisfied.

Referring back to FIG. 7, space for winding coil 20 is equally secured around the plurality of magnetic elements 18, and surfaces facing each other of every two adjacent magnetic elements 18 are provided substantially in parallel to each other. Thus, a large space for coils 20 can be secured and turns of coils 20 can be increased. As a result, large torque for driving impeller 10 to rotate can be generated. Further, copper loss that occurs in coils 20 can be reduced, thereby enhancing energy efficiency when impeller 10 is driven to rotate. The plurality of magnetic elements 18 may be formed in a cylindrical shape. In this case, a circumferential length of coils 20 can be minimized to reduce copper loss that occurs in coils 20, thereby enhancing energy efficiency when impeller 10 is driven to rotate.

An outline surface surrounding the plurality of magnetic elements 18 (a circle surrounding the peripheries of the plurality of magnetic elements 18 in FIG. 7) may correspond to an outline surface surrounding the plurality of permanent magnets 17 (a circle surrounding the peripheries of the plurality of magnetic elements 18 in FIG. 4), or the outline surface surrounding the plurality of magnetic elements 18 may be larger than the outline surface surrounding the plurality of permanent magnets 17. Further, it is preferable that magnetic element 18 be designed not to be magnetically saturated at maximum rating of pump 1 (a condition where torque for driving impeller 10 to rotate becomes maximum).

Voltages are applied to nine coils 20 in a power distribution system shifted by 120 degrees, for example. That is, nine coils 20 are divided into groups each including three coils. Voltages are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic element 18 having first coil 20 wound therearound (end surface on the impeller 10 side) becomes the N-pole during the period of 0 to 120 degrees, and becomes the S-pole during the period of 180 to 300 degrees. A Voltage VV is delayed in phase from a voltage VU by 120 degrees, and a voltage VW is delayed in phase from voltage VV by 120 degrees. Thus, rotating magnetic field can be formed by applying voltages VU, VV, VW to first to third coils 20, respectively, so that impeller 10 can be rotated by attractive force and repulsion force between the plurality of magnetic elements 18 and the plurality of permanent magnets 17 in impeller 10.

When impeller 10 is rotating at a rated rotation speed, attractive force between the magnetic elements 15 and 16 and the annular magnetic members 30 and 32 and attractive force between the plurality of permanent magnets 17 and the plurality of magnetic elements 18 are set to be balanced with each other substantially around a center of a movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be reduced. In addition, a surface of impeller 10 and a surface of an inner wall of housing 2 are not damaged (no projections and recesses in the surfaces) during the relative slide, and moreover, impeller 10 is readily levitated from housing 2 without contacting even when hydrodynamic force is small during low-speed rotation.

A number of grooves of hydrodynamic bearing 21 are formed in a surface of dividing wall X facing shroud 12 of impeller 10, and a number of grooves of hydrodynamic bearing 22 are formed in the inner wall of blood chamber 7 facing shroud 11. When a rotation speed of impeller 10 becomes higher than a prescribed rotation speed, a hydrodynamic bearing effect is produced between each of the grooves of hydrodynamic bearings 21 and 22 and impeller 10. As a result, drag is generated on impeller 10 from each of the grooves of hydrodynamic bearings 21 and 22, causing impeller 10 to rotate without contacting in blood chamber 7.

Figure 5:
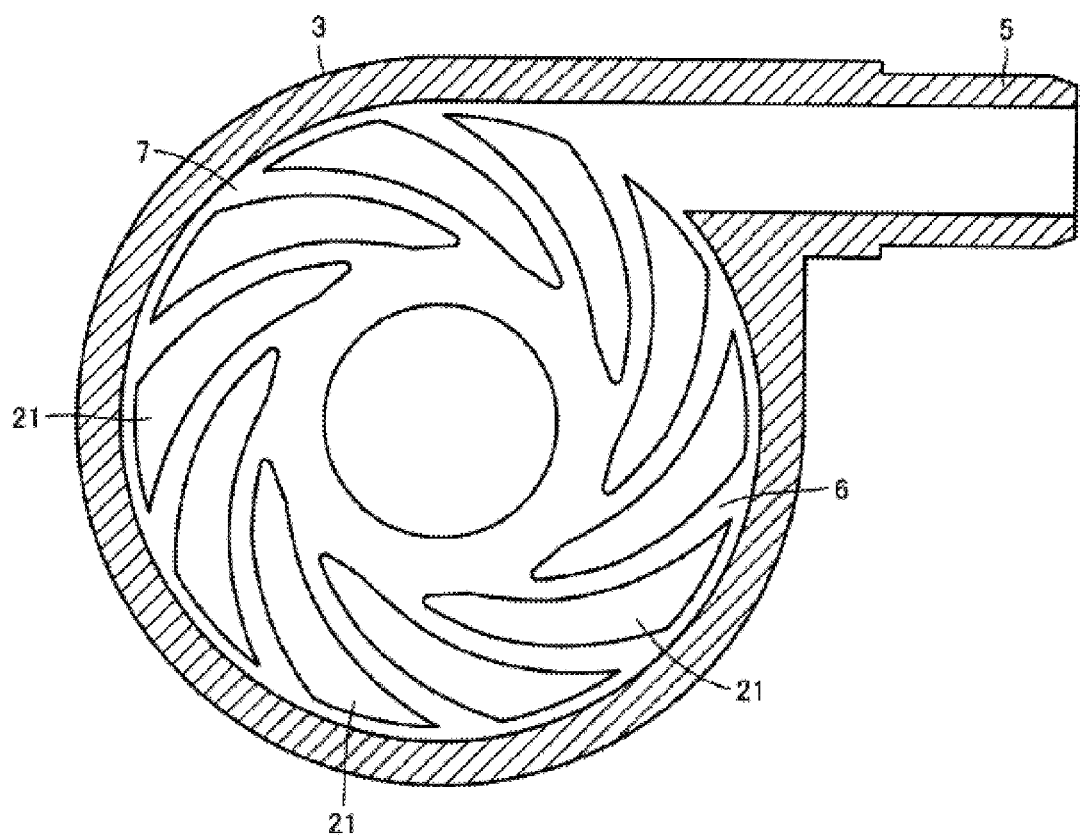
FIG. 5 shows yet another cross-section of the blood pump of FIG. 1.

Specifically, as shown in FIG. 5, each of the grooves of hydrodynamic bearing 21 are formed with a size corresponding to shroud 12 of impeller 10. Each groove of hydrodynamic bearing 21 is positioned with one end on an edge (circumference) of a circular portion slightly distant from a center of dividing wall 6. Each groove extends from the edge spirally (in other words, in a curved manner) toward a portion near an outer edge of dividing wall 6 such that the groove of the hydrodynamic bearing 21 gradually increases in width. Each of the grooves of hydrodynamic bearing 21 has substantially the same shape, and the grooves are arranged at substantially regular intervals. Each groove of hydrodynamic bearing 21 includes a concave portion. Each groove may have a depth of between about 0.005 to 0.400 mm. Between about 6 to 36 grooves may form hydrodynamic bearing 21.

In FIG. 5, ten grooves in an equiangular arrangement with respect to the central axis of impeller 10 form hydrodynamic bearing 21. Since the grooves of hydrodynamic bearing 21 have a so-called inward spiral groove shape, clockwise rotation of impeller 10 causes an increase in fluid pressure from an outer diameter portion toward an inner diameter portion of the grooves for hydrodynamic bearing 21. As a result, a repulsive force that acts as a hydrodynamic force is generated between impeller 10 and dividing wall 6.

In some embodiments, alternatively, or in addition to, providing grooves for hydrodynamic bearing 21 in dividing wall 6, grooves for hydrodynamic bearing 21 may be provided in a surface of shroud 12 of impeller 10. The hydrodynamic bearing effect produced between impeller 10 and the grooves of hydrodynamic bearing 21, causes impeller 10 to move away from dividing wall 6 and to rotate without contacting the dividing wall 6. Accordingly, a blood flow path is secured between impeller 10 and dividing wall 6, thus preventing occurrence of blood accumulation therebetween and the resultant thrombus. Further, in a normal state, the grooves of hydrodynamic bearing 21 perform a stirring function between impeller 10 and dividing wall 6, thus preventing occurrence of partial blood accumulation therebetween.

It is preferable that a corner portion of each of grooves for hydrodynamic bearing 21 be rounded to have R of at least 0.05 mm. As a result, occurrence of hemolysis can further be reduced.

Figure 6:
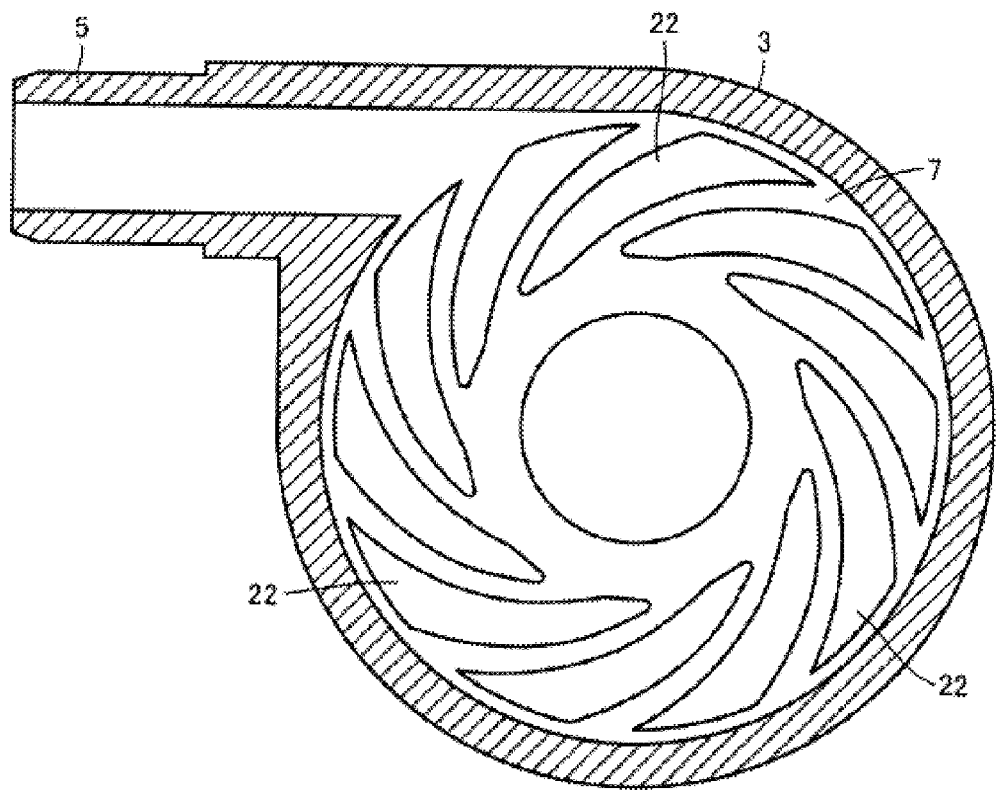
FIG. 6 shows yet another cross-section of the blood pump of FIG. 1.

As with the grooves of hydrodynamic bearing 21, as shown in FIG. 6, the grooves of hydrodynamic bearing 22 are each formed with a size corresponding to shroud 11 of impeller 10. Each groove of hydrodynamic bearing 22 has one end on an edge (circumference) of a circular portion slightly distant from a center of the inner wall of blood chamber 7. The groove extends spirally (in other words, in a curved manner) toward a portion near an outer edge of the inner wall of blood chamber 7 such that the groove gradually increases in width. Each of the grooves has substantially the same shape. The grooves are arranged at substantially regular intervals. Each groove of hydrodynamic bearing 22 includes a concave portion. Each groove may have a depth of between about 0.005 to 0.4 mm. It is preferable that about 6 to 36 grooves form hydrodynamic bearing 22. In FIG. 6, ten grooves forming hydrodynamic bearing 22 are equiangularly arranged with respect to the central axis of impeller 10.

Alternatively, or in addition to, providing the grooves of hydrodynamic bearing 22 in the inner wall of blood chamber 7, the grooves of hydrodynamic bearing 22 may be provided in a surface of shroud 11 of impeller 10. It is preferable that a corner portion of each of grooves of hydrodynamic bearing 22 be rounded to have R of at least 0.05 mm. As a result, occurrence of hemolysis can further be reduced The hydrodynamic bearing effect produced between impeller 10 and the grooves for hydrodynamic bearing 22 causes impeller 10 to move away from the inner wall of blood chamber 7 and rotates without contacting the inner wall. In addition, when pump unit 1 is subjected to external impact or when the hydrodynamic force generated by hydrodynamic bearing 21 becomes excessive, impeller 10 can be prevented from being in close contact with the inner wall of blood chamber 7. The hydrodynamic force generated by hydrodynamic bearing 21 may be different from the hydrodynamic force generated by hydrodynamic bearing 22.

It is preferable that impeller 10 rotate in a state where a gap between shroud 12 of impeller 10 and dividing wall 6 is substantially equal to a gap between shroud 11 of impeller 10 and the inner wall of blood chamber 7. If one of the gaps becomes narrower due to serious disturbance such as fluid force acting on impeller 10, it is preferable that grooves of hydrodynamic bearing 21 and 22 have different shapes so that the hydrodynamic force generated by the hydrodynamic bearing on the narrower side becomes higher than the hydrodynamic force generated by the other hydrodynamic bearing to make the gaps substantially equal to each other.

While each groove of hydrodynamic bearings 21 and 22 has the inward spiral groove shape shown in FIGS. 5-6, grooves having another shape may be used. Nevertheless, for blood circulation, it is preferable to employ grooves having the inward spiral groove shape, which allows for a smooth flow of blood.

As mentioned above, it is contemplated that the blood inlet port 4 may be configured and/or arranged to minimize or prevent the formation of thrombosis within (i.e., internal) the blood inlet port 4, and also to minimize turbulence at a fluid interface between the blood inlet port 4 and the blood chamber 7. In general, it is contemplated that thrombosis formation may occur due to a vortex forming in or within one or both of blood inlet port 4 and the blood chamber 7 in a location near or adjacent blood inlet port 4, and/or due to stress or forces imparted on blood as it transitions into a spinning motion once it reaches the impeller 10.

FIGS. 8-15 depict embodiments of pumps using one or more annular magnetic members of a magnetic suspension system to maintain a size of a gap between an impeller and a chamber wall of a housing at high impeller speeds. Theses pumps may be configured as those described in FIGS. 1-7 above. The annular magnetic members may correspond to the annular magnetic members 30 and 32 described herein. The magnetic suspension systems are often made up of magnetic elements within the impeller, annular magnetic members embedded within a housing of the pump, a stator motor, and/or hydrostatic bearings formed in the housing. Embodiments maintain this gap size by producing a lower net attractive force at an outer or distal portion of the impeller than at an inner or proximal portion of the impeller. In some embodiments this net attractive force relationship is achieved by decreasing the attractive force at the outer portion or by producing a repulsive force at the outer portion. Other embodiments achieve the greater inner attractive force by increasing the attractive force at the inner portion of the impeller. In other embodiments, the gap may be maintained by using electromagnets as the annular magnetic members and utilizing active magnetic control to adjust the magnetic forces as impeller speeds and/or gap size change. Alternative methods of increasing and/or maintaining the gap size at high impeller speeds may also include increasing the gap between the motor stator and the motor magnet, although his may decrease the efficiency of the motor. It will be appreciated that combinations of the techniques described herein may be used to further adjust and/or maintain the gap size.

Figure 8:
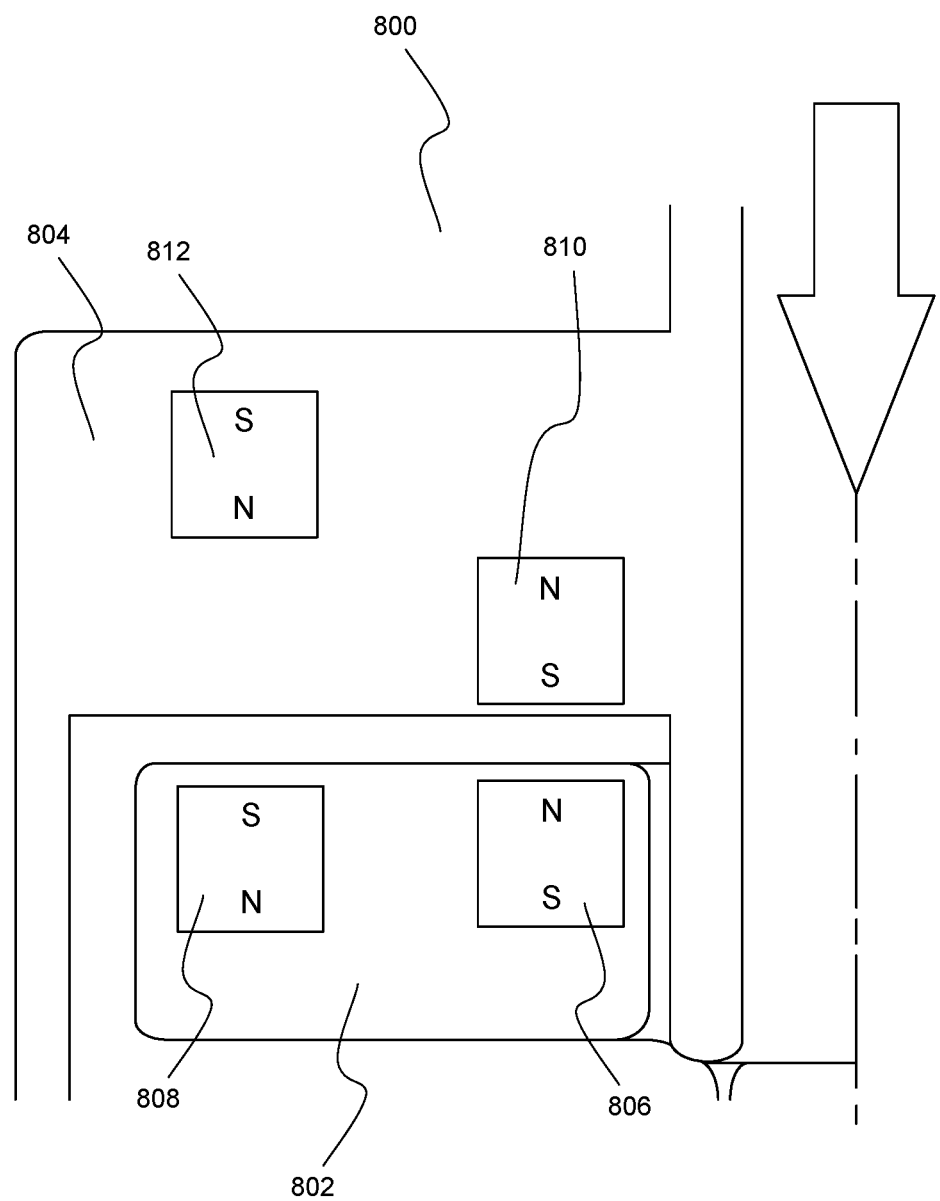
FIG. 8 shows one embodiments of magnetic stabilization features of a blood pump according to embodiments.
Figure 9:
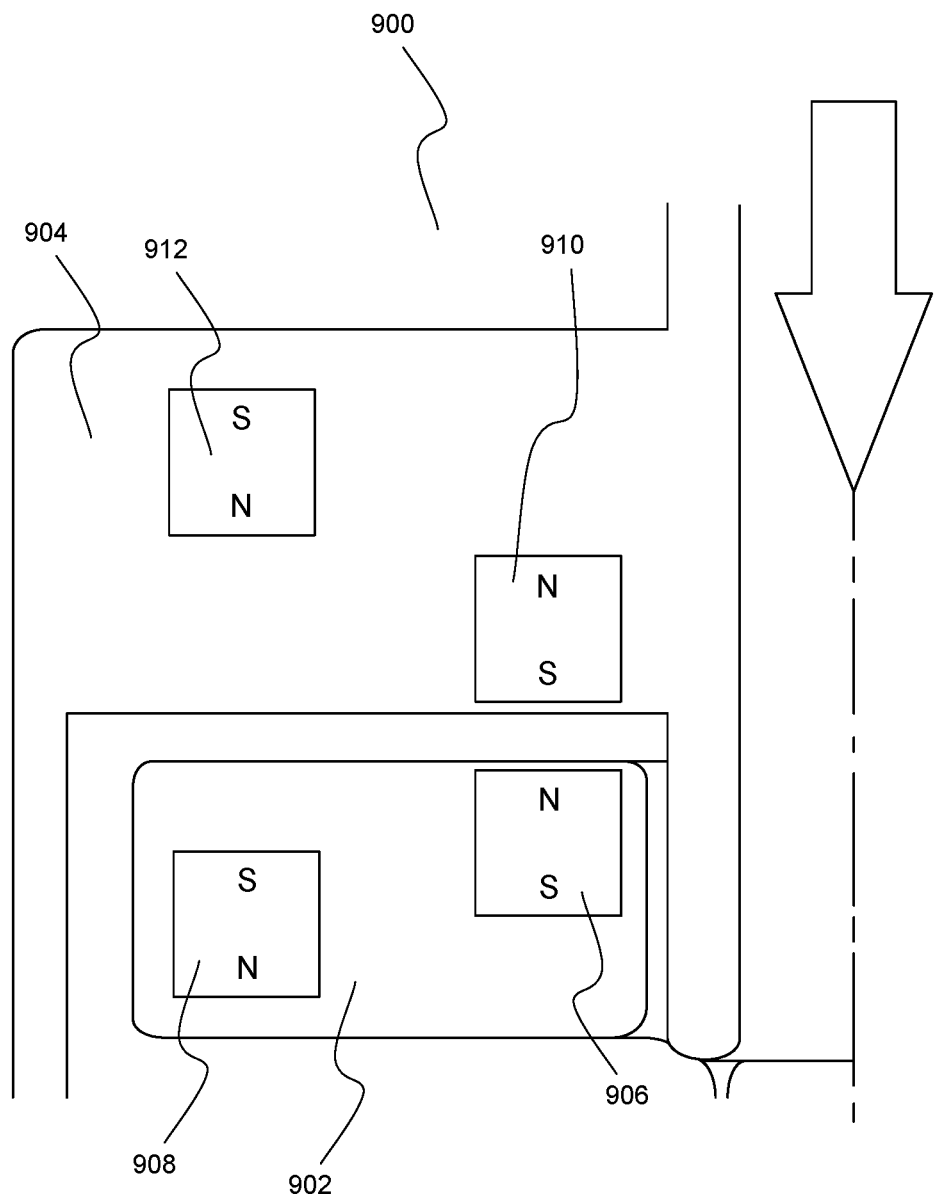
FIG. 9 shows one embodiments of magnetic stabilization features of a blood pump according to embodiments.

FIGS. 8 and 9 depict systems that decrease the outer annular magnetic member's magnetic force to create a greater net magnetic attraction at the inner annular magnetic member. In FIG. 8, a pump 800 having a housing 802 is shown. An impeller 804 is shown having a plurality of magnetic elements embedded therein. The impeller is configured to rotate within the housing 802. Here, an inner magnetic element 806 and an outer magnetic element 808 are embedded within impeller 804. One or more annular magnetic members may be embedded within housing 802. For example, an inner annular magnetic member 810 and an outer annular magnetic member 812 are embedded within a side wall of the housing 802. As shown here, by making a distance between the inner annular magnetic member 810 and inner magnetic element 806 less than a distance between outer annular magnetic member 812 and outer magnetic element 808, the net attractive force along the outer edge of impeller 802 may be decreased and/or made lower than the net attractive force at an inner portion of the impeller 802. This lessened attractive force results in a reduction of negative stiffness at the outer annular magnetic member 812 and an increase in the gap between the impeller 802 and the inner wall of the housing 804. Making the distance between the inner magnets smaller than the distance between the outer magnets can be achieved by moving the inner annular magnetic member 810 closer to the impeller, by moving the outer annular magnetic member 812 away from the impeller, and/or by a combination of both.

In some embodiments, making the distance between the inner magnets smaller than the distance between the outer magnets can be achieved by changing a position of the inner magnet and/or the outer magnet relative to the impeller as shown in FIG. 9. For example, a pump 900 may have a housing 904 and an impeller 906 such as described in FIG. 8. An inner magnet 906 of the impeller 902 may be moved closer to an inner annular magnetic member 910 within the housing 904 and/or an outer magnet 908 may be moved away from an outer annular magnetic member 912. In some embodiments, one or more of both the housing magnetic members 810 and 812 and the impeller magnetic elements 806 and 808 may be positioned to create the larger distance between the outer magnets than the inner magnets. In some embodiments, the net force difference between the inner and outer portions of the impeller may be attained by decreasing the attractive force at the outer annular magnetic member, such as by reducing the magnet size and/or otherwise reducing the strength of the outer annular magnetic member 912.

Figure 10:
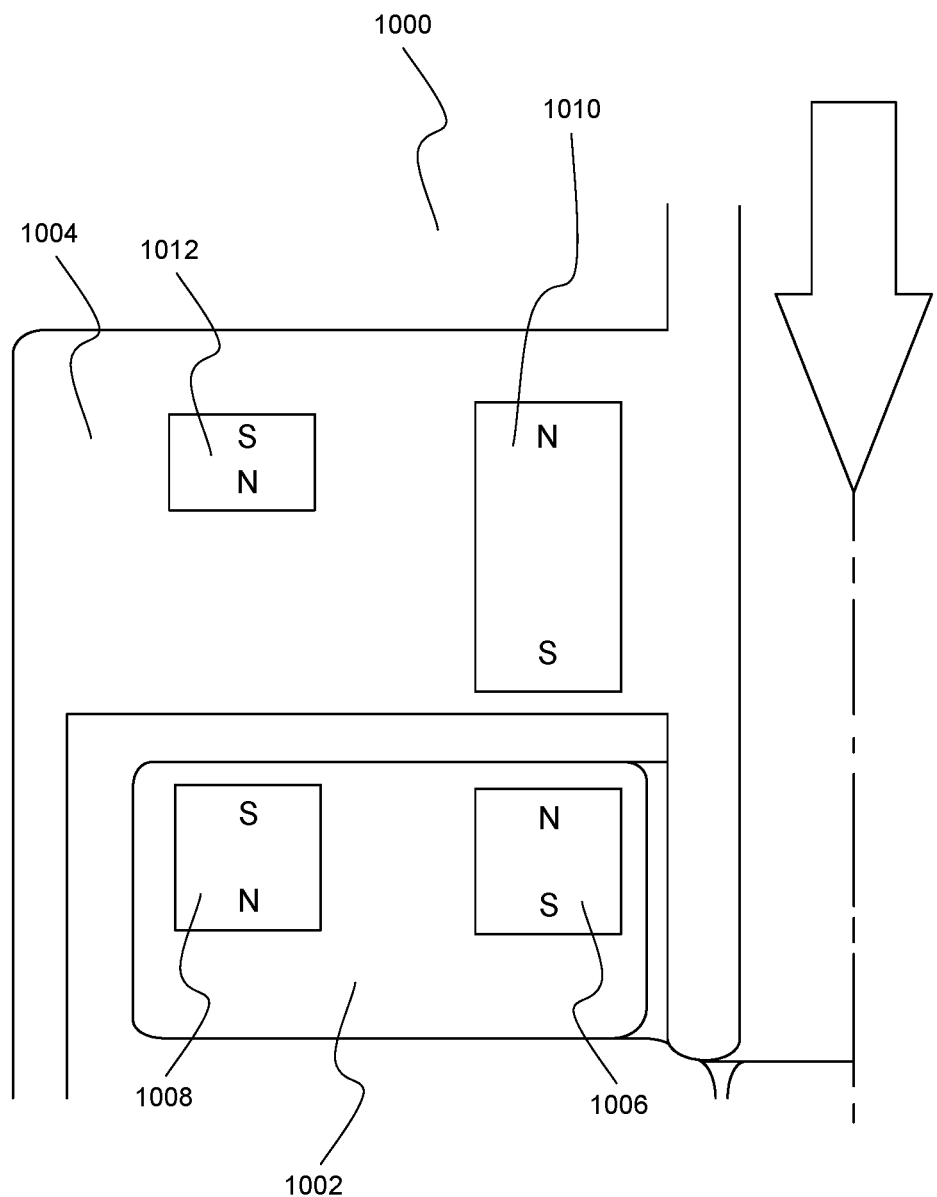
FIG. 10 shows one embodiments of magnetic stabilization features of a blood pump according to embodiments.
Figure 11:
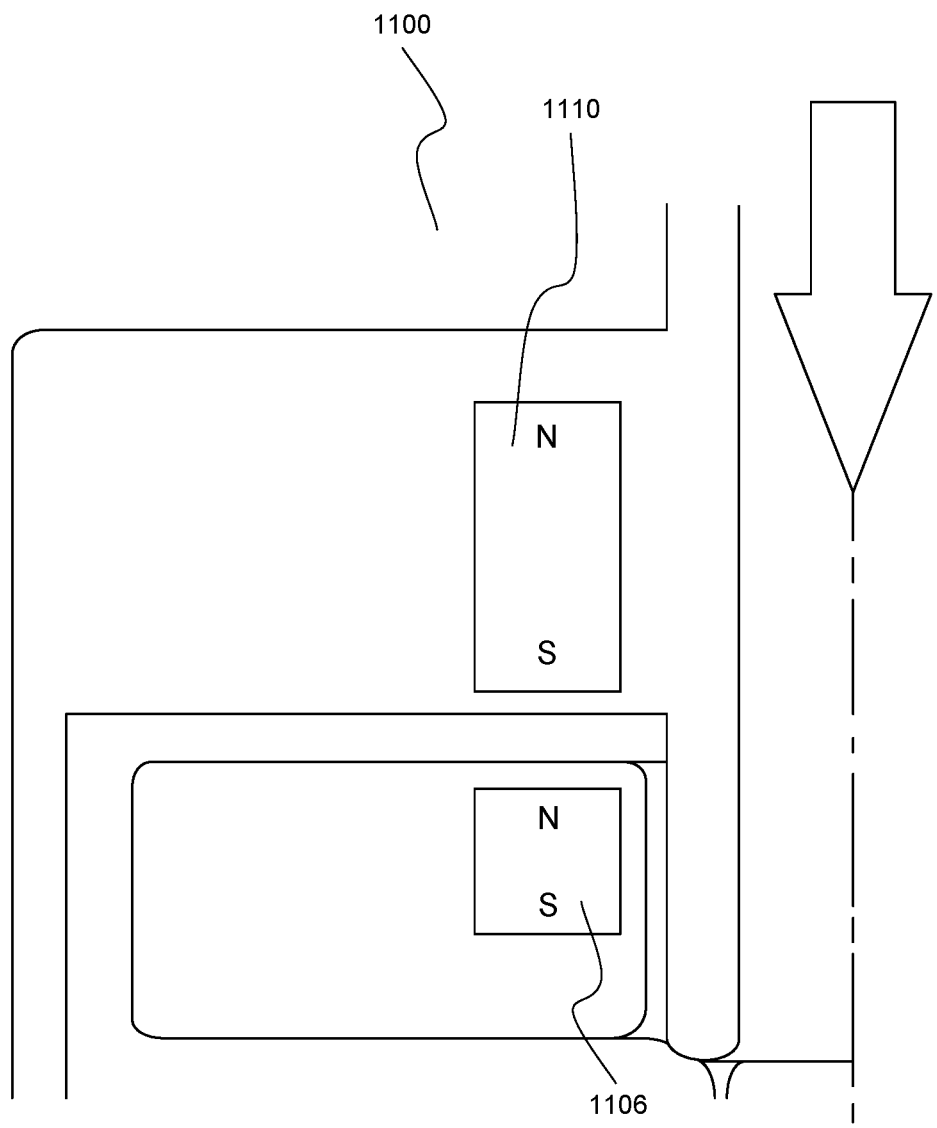
FIG. 11 shows one embodiments of magnetic stabilization features of a blood pump according to embodiments.

FIGS. 10 and 11 depict embodiments of pumps that increase a magnetic force of an inner annular magnetic member and decrease or eliminate a magnetic force of an outer annular magnetic member. For example, in FIG. 10, a pump 1000 is shown having an impeller 1002, housing 1004, an inner magnetic element 1006, and an outer magnetic element 1008 as described above with regard to FIG. 8. Pump 1000 may include an inner annular magnetic member 1010 having a net magnetic attraction with the inner magnetic element 1006 that is greater than a net magnetic attraction between an outer annular magnetic member 1012 and the outer magnetic element 1008. In pump 1000, this is done by increasing the magnetic force of the inner annular magnetic member 1010 in combination with reducing the magnetic force of the outer annular magnetic member 1012 and/or by increasing the distance between the outer annular magnetic member 1012 and the outer magnetic element 1008. The increase in magnetic force of the inner annular magnetic member may be realized by increasing the magnet volume and/or by using a stronger magnet. In some embodiments, the magnetic force of the inner annular magnetic member 1010 may be increased sufficiently such that the outer annular magnetic member 1012 and/or outer magnetic element 1008 may be eliminated. For example, FIG. 11 shows a pump 1100 having only a strong inner annular magnetic member 1110 and an inner magnetic element 1106.

Figure 12:
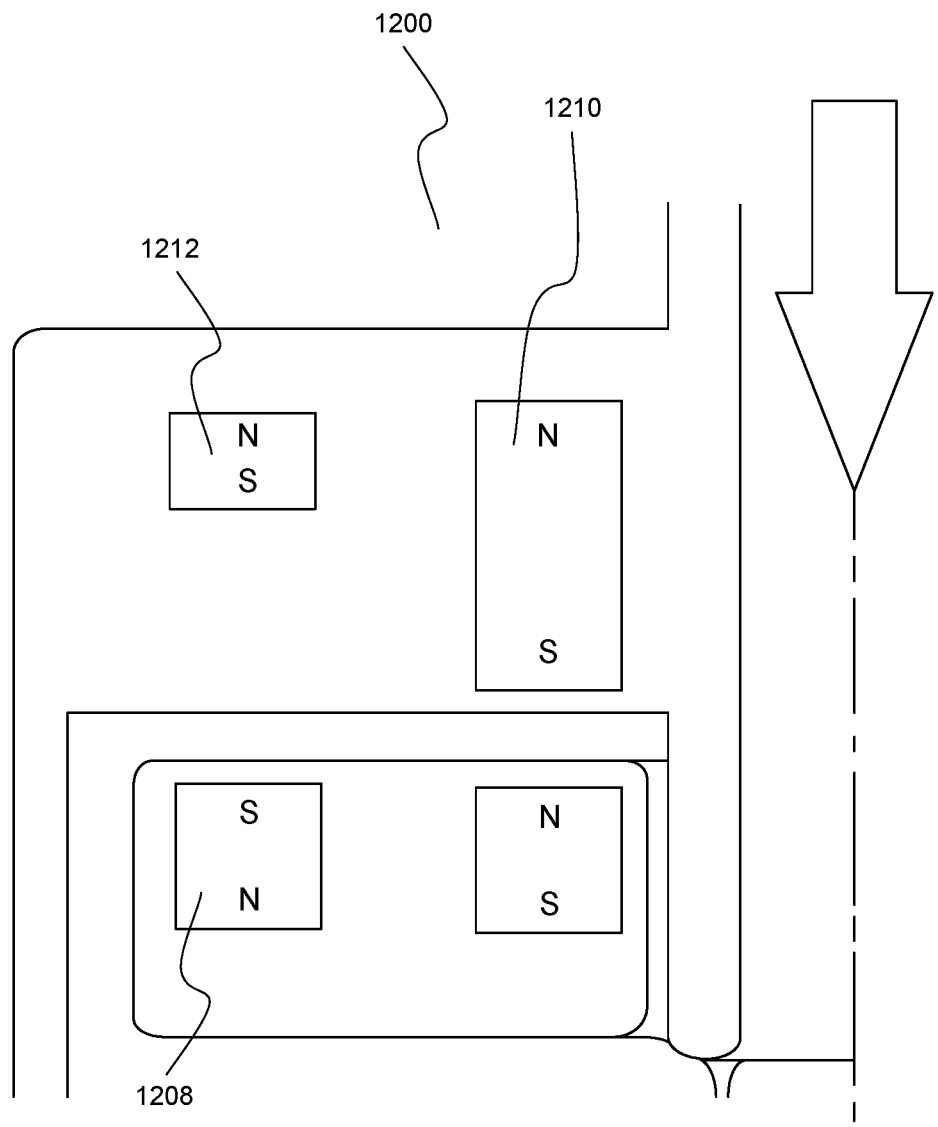
FIG. 12 shows one embodiments of magnetic stabilization features of a blood pump according to embodiments.

In some embodiments, the gap between the impeller and the housing may be maintained by increasing the attractive force of the inner annular magnetic member while using an opposite polarity magnet as the outer annular magnetic member to create a repulsive force on the outer edge of the impeller and to increase the impeller suspension stiffness. For example, FIG. 12 shows a pump 1200 having an inner annular magnetic member 1210 having a sufficiently high attractive magnetic force and an outer annular magnetic member 1212 that has a polarity relative to an outer magnetic element 1208 to create a repulsive force that serves to maintain the gap size, even at high impeller speeds.

Figure 13:
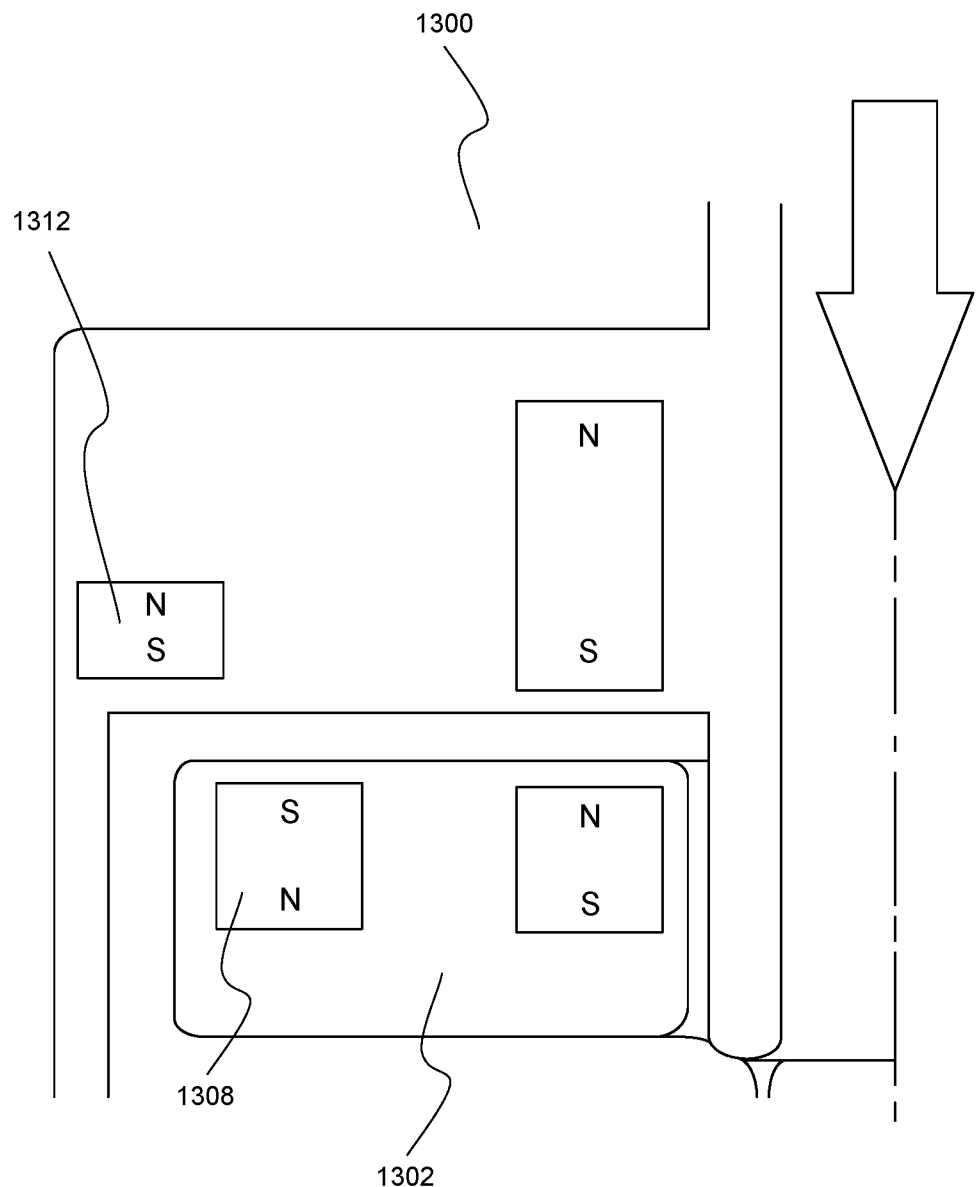
FIG. 13 shows one embodiments of magnetic stabilization features of a blood pump according to embodiments.

FIG. 13 shows one embodiment of a pump 1300 where a diameter of an outer annular magnetic member 1312 is increased to be larger than a diameter of an outer magnetic element 1308 on an impeller 1302 and/or to extend radially beyond at least a portion of the outer magnetic element 1308. The outer annular magnetic member 1312 also has a polarity selected to create a net repulsive force with the outer magnetic element 1308. When the outer annular magnetic member 1312 extends beyond at least a portion of the outer magnetic element 1308, the repulsive force has a force component toward the rotational axis of the impeller 1302, which increases the radial stiffness. The impeller rotation center shifts toward an outlet side of pump 1300 when the flow rate is high. The repulsive force of the rotational axis direction increases as the impeller is pushed toward the outlet side, compensating against pump pressure distribution due to the high flow rate. Thus, the repulsive force produce by the outer annular magnetic member 1312 helps maintain the impeller position, and thus gap size, as impeller speeds increase.

Figure 14:
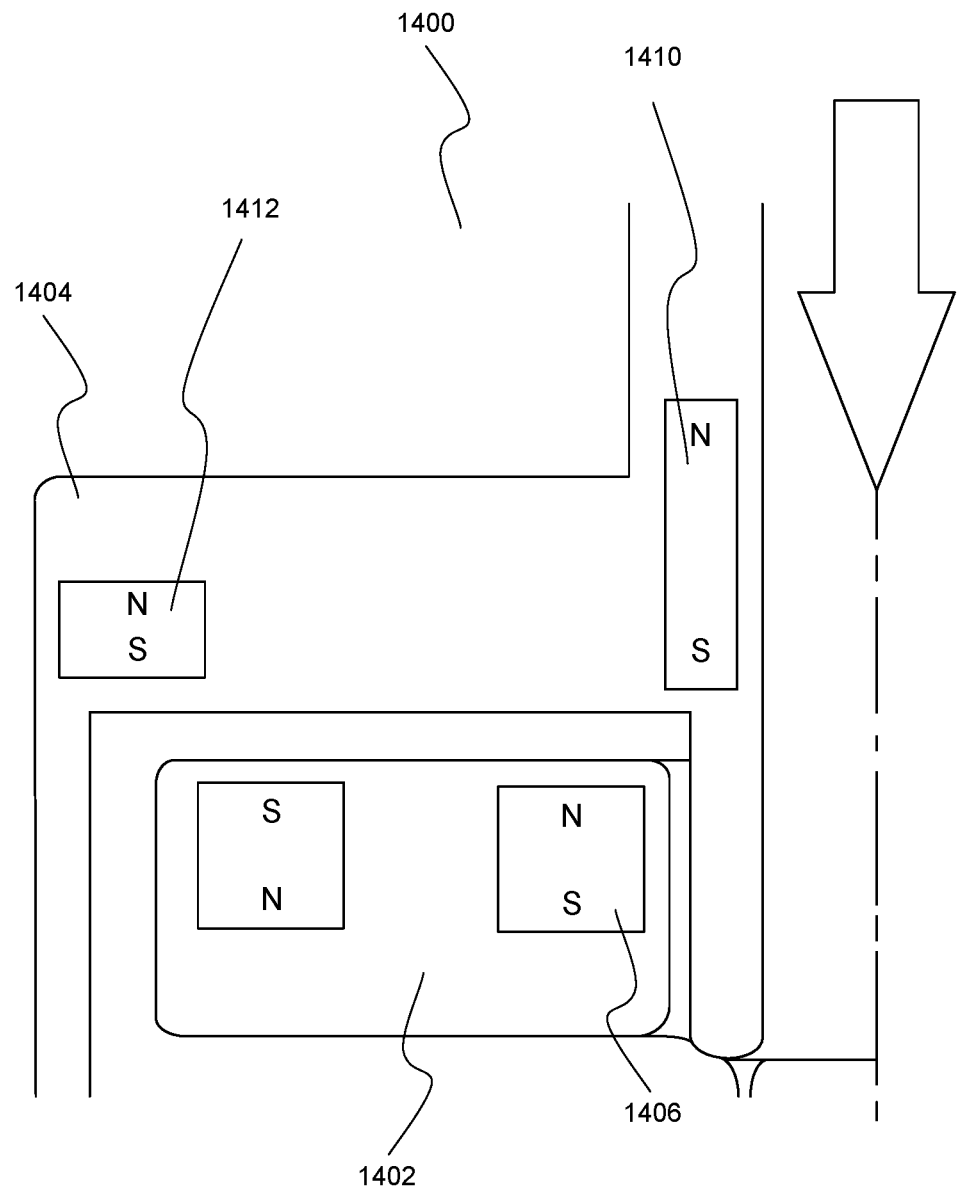
FIG. 14 shows one embodiments of magnetic stabilization features of a blood pump according to embodiments.

In some embodiments, reduction of a diameter of an inner annular magnetic member may be used in conjunction with increasing a diameter of an outer annular magnetic member, resulting in an increase in the radial stiffness of the magnetic suspension system of the pump. For example, FIG. 14 shows a pump 1400 having an outer annular magnetic member 1412 of increased diameter and an inner magnetic member 1410 having a reduced diameter. By reducing the diameter of the inner annular magnetic member 1410 such that the inner annular magnetic member 1410 is positioned at least partially inward of the inner magnetic element 1406, a thickness of a pump housing 1404 may be reduced by putting an inner annular magnetic member 1410 of increased size within dead space of a pump inflow conduit 1414. This positioning results in an increase in the negative stiffness of the magnetic suspension system. The radial component of the repulsive force of the outer annular magnetic member maintains the impeller radial stiffness as the position of the inner annular magnetic member 1410 increases the negative stiffness. Additionally, the inward position of the inner annular magnetic member 1410 increases the magnetic resistance while reducing the magnetic flux, and thus, the net attractive force acting on the impeller 1402. The repulsive force of the outer annular magnetic member 1412 helps compensate for the reduction of attractive force of the inner annular magnetic member 1410 to maintain the gap size between the housing 1404 and the impeller 1402.

Figure 15:
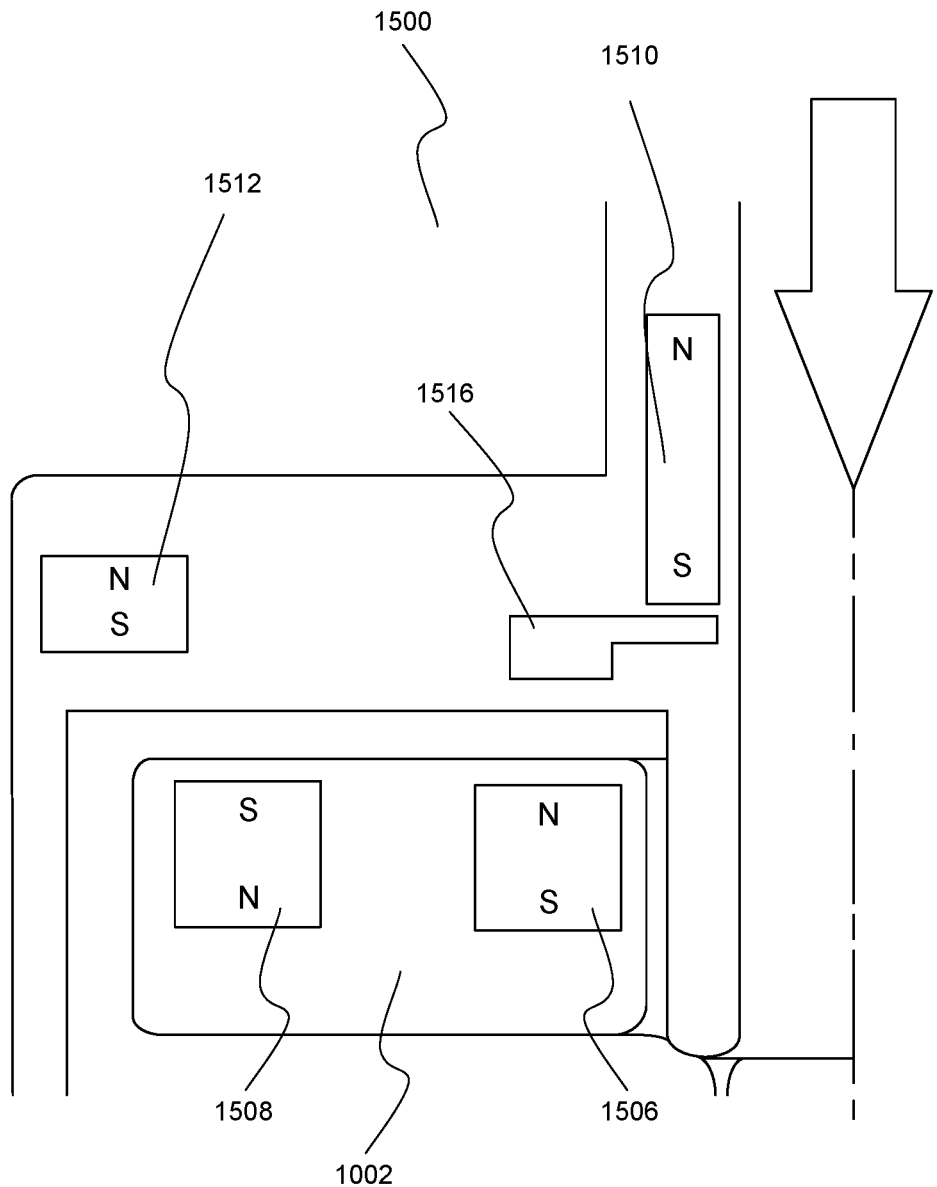
FIG. 15 shows one embodiments of magnetic stabilization features of a blood pump according to embodiments.

In some embodiments, a ferromagnetic ring, such as a steel ring, may be positioned between an inner annular magnetic member and an inner magnetic element when the inner annular magnetic member has a diameter positioned inward of an inner magnetic element on an impeller. FIG. 15 shows a pump 1500 having an outer annular magnetic member 1512 extending radially beyond an outer magnetic element 1508 and an inner annular magnetic member 1510 positioned inward of an inner magnetic element 1506. Pump 1500 also includes a ferromagnetic ring 1516 positioned between inner annular magnetic member 1510 and inner magnetic element 1506. The ring 1516 skews the magnetic flux such that the attractive force from the inner annular magnetic member 1510 is better directed to act upon the inner magnetic element 1506.

The invention has now been described in detail for the purposes of clarity and understanding. However, it will be appreciated that certain changes and modifications may be practiced within the scope of the disclosure.

What is claimed is:

1. A centrifugal blood pump, comprising:
   a housing that defines an inlet passage, a chamber, and an outlet passage;
   an impeller rotatably positioned in the chamber to transfer blood from the inlet passage through the chamber and to the outlet passage, the impeller comprising an inner portion and an outer portion;
   a plurality of impeller magnets embedded in the impeller such that the impeller and the plurality of impeller magnets rotate together within the chamber, the plurality of impeller magnets comprising an inner impeller magnet and an outer impeller magnet relative to a central axis of the impeller;

a motor to control movement of the impeller in the chamber, the motor being positioned adjacent the chamber and separated from the chamber by a partition member;

an inner annular magnetic member embedded in a wall of the housing opposite the partition member; and an outer annular magnetic member embedded in the wall of the housing opposite the partition member, wherein a first net magnetic force between the inner annular magnetic member and the inner impeller magnet exhibits greater attraction than a second net magnetic force between the outer annular member and the outer impeller magnet.

2. The centrifugal blood pump according to claim 1, wherein:
a distance between the outer impeller magnet and the outer annular magnetic member is greater than a distance between the inner impeller magnet and the inner annular magnetic member.

3. The centrifugal blood pump according to claim 1, wherein:
the inner annular magnetic member produces a greater magnetic force than the outer annular magnetic member.

4. The centrifugal blood pump according to claim 1, wherein:
the inner annular magnetic member has a greater volume than the outer annular magnetic member.

5. The centrifugal blood pump according to claim 1, wherein:
the first net magnetic force is an attractive force and the second net magnetic force is a repulsive force.

6. The centrifugal blood pump according to claim 1, wherein:
at least a portion of the outer annular magnetic member extends radially beyond at least a portion of the outer impeller magnet, and
a net repulsive force is exhibited between the outer annular magnetic member and the outer impeller magnet.

7. The centrifugal blood pump according to claim 6, wherein:
at least a portion of the inner annular magnetic member is disposed radially inward of the inner impeller magnet; and
a net attractive force is exhibited between the inner annular magnetic member and the inner impeller magnet.

8. The centrifugal blood pump according to claim 1, further comprising:
a ferromagnetic ring disposed between the inner annular magnetic member and the inner impeller magnet.

9. A centrifugal blood pump, comprising:
a housing that defines an inlet passage, a chamber, and an outlet passage;
an impeller rotatably positioned in the chamber to transfer blood from the inlet passage through the chamber and to the outlet passage;
a plurality of impeller magnets embedded in the impeller such that the impeller and the plurality of impeller magnets rotate together within the chamber;
a motor to control movement of the impeller in the chamber, the motor being positioned adjacent the chamber and separated from the chamber by a partition member; and
at least one annular magnetic member embedded in a wall of the housing opposite the partition member, wherein a first net magnetic force between the at least one annular magnetic member and a proximal portion the plurality of impeller magnets exhibits greater attraction than a second net magnetic force between the at least one annular magnetic member and a distal portion of the plurality of impeller magnets, the proximal portion and the distal portion being relative to a central axis of the impeller.

10. The centrifugal blood pump of claim 9, wherein:
the plurality of impeller magnets comprises an inner impeller magnet and an outer impeller magnet; and
the inner annular magnetic member produces a greater magnetic force than the outer annular magnetic member.

11. The centrifugal blood pump of claim 9, wherein:
the plurality of impeller magnets comprises an inner impeller magnet and an outer impeller magnet; and
a distance between the outer impeller magnet and the outer annular magnetic member is greater than a distance between the inner impeller magnet and the inner annular magnetic member.

12. The centrifugal blood pump of claim 9, wherein:
the first net magnetic force is an attractive force and the second net magnetic force is a repulsive force.

13. The centrifugal blood pump of claim 9, wherein:
the plurality of impeller magnets comprises an inner impeller magnet and an outer impeller magnet;
at least a portion of the outer annular magnetic member extends radially beyond at least a portion of the outer impeller magnet, and
a net repulsive force is exhibited between the outer annular magnetic member and the outer impeller magnet.

14. The centrifugal blood pump of claim 9, further comprising:
a ferromagnetic ring disposed between the inner annular magnetic member and the inner impeller magnet.

15. A centrifugal blood pump, comprising:
a housing that defines an inlet passage, a chamber, and an outlet passage;
an impeller rotatably positioned in the chamber to transfer blood from the inlet passage through the chamber and to the outlet passage, the impeller comprising an inner portion and an outer portion relative to a central axis of the impeller;
at least one impeller magnet embedded in the impeller such that the impeller and at least one magnetic member rotate together within the chamber;
a motor to control movement of the impeller in the chamber, the motor being positioned adjacent the chamber and separated from the chamber by a partition member; and
at least one annular magnetic member embedded in a side of the housing opposite the partition member, wherein a first force exhibited on the inner portion has a greater attraction than a second force exhibited on the outer portion of the impeller, wherein the first force and the second force each result from interactions between the at least one impeller magnet and the at least one annular magnetic member.

16. The centrifugal blood pump of claim 15, wherein:
each of the at least one impeller magnet is disposed on the inner portion of the impeller and each of the at least one annular magnet is disposed on an inner portion of the housing.

17. The centrifugal blood pump of claim 15, wherein:
the first force is an attractive force and the second force is a repulsive force.

18. The centrifugal blood pump of claim 15, wherein:
the at least one impeller magnet comprises an inner impeller magnet and an outer impeller magnet;
at least a portion of the outer annular magnetic member extends radially beyond at least a portion of the outer impeller magnet, and
a net repulsive force is exhibited between the outer annular magnetic member and the outer impeller magnet.

19. The centrifugal blood pump of claim 18, wherein:
at least a portion of the inner annular magnetic member is disposed radially inward of the inner impeller magnet; and
a net attractive force is exhibited between the inner annular magnetic member and the inner impeller magnet.

20. The centrifugal blood pump of claim 15, wherein:
a distance between the outer impeller magnet and the outer annular magnetic member is greater than a distance between the inner impeller magnet and the inner annular magnetic member.

* * * * *